(12) United States Patent
Chang et al.

(10) Patent No.: US 7,740,727 B2
(45) Date of Patent: *Jun. 22, 2010

(54) ELASTIC COMPOSITE FOR A DISPOSABLE ABSORBENT GARMENT, AND A SYSTEM AND PROCESS FOR MAKING THE ELASTIC COMPOSITE AND A GARMENT HAVING THE ELASTIC COMPOSITE

(75) Inventors: Kuo-Shu Edward Chang, Charlotte, NC (US); Anne Smid, Wolvega (NL); Patrick King Yu Tsang, Tuen Mun (CN); Andrew C. Wright, Derbyshire (GB)

(73) Assignee: DSG Technology Holdings, Ltd, Tortola (VG)

( * ) Notice: Subject to any disclaimer, the term of this patent is extended or adjusted under 35 U.S.C. 154(b) by 246 days.

This patent is subject to a terminal disclaimer.

(21) Appl. No.: 11/982,349

(22) Filed: Oct. 31, 2007

(65) Prior Publication Data

US 2008/0176026 A1    Jul. 24, 2008

(51) Int. Cl.
B32B 37/00    (2006.01)
(52) U.S. Cl. .................. 156/177; 156/178; 156/179; 156/200
(58) Field of Classification Search ............ 156/200, 156/196, 463, 176, 177, 178, 179
See application file for complete search history.

(56) References Cited

U.S. PATENT DOCUMENTS

| | | | | |
|---|---|---|---|---|
| 1,195,949 A | * | 8/1916 | Carney | 156/168 |
| 2,718,254 A | * | 9/1955 | Carlson | 156/172 |
| 2,901,395 A | | 9/1959 | Hirschy et al. | |
| 3,041,230 A | * | 6/1962 | Diehl | 156/172 |
| 3,627,621 A | | 12/1971 | Mowers | |
| 3,649,411 A | * | 3/1972 | Bolles | 156/391 |
| 3,800,796 A | | 4/1974 | Jacob | |
| 3,801,401 A | | 4/1974 | Cope et al. | |
| 4,284,454 A | | 8/1981 | Joa | |
| 4,527,990 A | | 7/1985 | Sigl | |

(Continued)

FOREIGN PATENT DOCUMENTS

EP    1188427    3/2002

(Continued)

*Primary Examiner*—Jeff H Aftergut
(74) *Attorney, Agent, or Firm*—Alberto Q. Amatong, Jr.; The Amatong Law Firm, PLLC

(57) ABSTRACT

A method is provided for making an elastic composite for incorporation into a disposable absorbent garment. An elastic element applicator is provided that is configured to move a section of a continuous strand of elastic element generally about a plane. A first web of material is conveyed in a first web moving direction such that the first web intersects the plane. Then, the applicator is operated to move the elastic element about the plane, thereby applying the section of elastic element onto the first web along a direction generally transverse to the web moving direction and such that the first web draws the continuous elastic strand from the elastic element applicator as the first web is conveyed away from the plane. The elastic element applicator may be in the form of a spin cylinder or bracket that is operated to spin the elastic element about the moving first web, thereby applying the elastic element on the first web.

27 Claims, 14 Drawing Sheets

U.S. PATENT DOCUMENTS

| | | | |
|---|---|---|---|
| 4,602,973 A * | 7/1986 | Holroyd et al. | 156/177 |
| 4,642,151 A | 2/1987 | Coenen | |
| 4,726,874 A | 2/1988 | VanVliet | |
| 5,127,981 A | 7/1992 | Straub et al. | |
| 5,221,390 A * | 6/1993 | Persson et al. | 156/164 |
| 5,429,694 A | 7/1995 | Herrmann | |
| 5,531,729 A | 7/1996 | Coles et al. | |
| 5,531,850 A | 7/1996 | Herrmann | |
| 5,591,152 A | 1/1997 | Buell et al. | |
| 5,628,741 A | 5/1997 | Buell et al. | |
| 5,685,873 A | 11/1997 | Bruemmer | |
| 5,779,691 A | 7/1998 | Schmitt | |
| 5,807,371 A | 9/1998 | Toyoda et al. | |
| 5,938,652 A | 8/1999 | Sauer | |
| 6,086,571 A | 7/2000 | Guevara et al. | |
| 6,123,694 A | 9/2000 | Pieniak et al. | |
| 6,146,369 A | 11/2000 | Hartman et al. | |
| 6,336,922 B1 | 1/2002 | VanGompel et al. | |
| 6,340,782 B1 | 1/2002 | Kling et al. | |
| 6,419,667 B1 | 7/2002 | Avalon et al. | |
| 6,425,430 B1 | 7/2002 | Ward et al. | |
| 6,454,750 B1 | 9/2002 | Vogt et al. | |
| 6,454,752 B1 | 9/2002 | Huang et al. | |
| 6,649,001 B2 | 11/2003 | Heden et al. | |
| 6,855,223 B2 | 2/2005 | Johnson | |
| 7,361,246 B2 * | 4/2008 | Chang et al. | 156/177 |
| 2001/0039700 A1 | 11/2001 | Krueger | |
| 2002/0038110 A1 | 3/2002 | Kusibojoska et al. | |
| 2002/0151863 A1 | 10/2002 | Toyoshima | |
| 2002/0177829 A1 | 11/2002 | Fell et al. | |
| 2003/0064652 A1 | 4/2003 | Heden et al. | |
| 2003/0069557 A1 | 4/2003 | Driskell et al. | |
| 2003/0083634 A1 | 5/2003 | Fernfors | |
| 2003/0089454 A1 | 5/2003 | Johnson | |
| 2003/0109844 A1 | 6/2003 | Gibbs | |
| 2003/0139725 A1 | 7/2003 | Gibbs | |
| 2003/0144643 A1 | 7/2003 | Jarpenberg et al. | |
| 2005/0095942 A1 | 5/2005 | Mueller et al. | |
| 2005/0131373 A1 | 6/2005 | Wright et al. | |
| 2006/0139311 A1 | 6/2006 | Chang et al. | |

FOREIGN PATENT DOCUMENTS

| | | | |
|---|---|---|---|
| EP | 1520569 | | 4/2005 |
| JP | 2002-192641- | * | 1/2002 |
| JP | 2002-192641 | | 7/2002 |
| WO | WO 9519258 A1 | | 7/1995 |
| WO | 01/00915 | | 1/2001 |
| WO | WO 0232364 A1 | | 4/2002 |
| WO | WO/03/041627 | | 5/2003 |
| WO | WO 03017903 | | 6/2003 |
| WO | WO 2004/087416 | | 10/2004 |
| WO | 2005/060910 | | 7/2005 |

\* cited by examiner

ELASTIC COMPOSITE FOR A DISPOSABLE ABSORBENT GARMENT, AND A SYSTEM AND PROCESS FOR MAKING THE ELASTIC COMPOSITE AND A GARMENT HAVING THE ELASTIC COMPOSITE

The present application claims the benefit of the filing date of U.S. patent application Ser. No. 11/021,424, filed Dec. 23, 2004, now U.S. Pat. No. 7,361,246, which claims the benefit of the filing date of U.S. Provisional Application Ser. No. 60/532,480, filed on Dec. 24, 2003. The above applications are thereby incorporated by reference for all purposes and made a part of the present disclosure.

BACKGROUND OF THE INVENTION

The present invention relates generally to disposable absorbent garments or articles such as baby diapers and training pants. More particularly, the present invention relates to an elastic component that can be employed in one or more areas of the garment. The present invention also relates to a system and method of making the elastic component and a garment employing the elastic component.

Disposable absorbent garments contemplated by the invention include disposable diapers, disposable pull-on garments, and the like. These garments are worn about the lower torso or waist of the user so as to receive and contain urine and other bodily wastes. The benefits provided by the use of a disposable diaper on an infant are well known and its use has become widespread in the past several decades. Disposable pull-on garments include training pants, pull-on diapers, disposable underwear, and adult incontinence garments. It is generally expected that the user of any one of these garments will be able to put on and take off the garment on his/her own. As for training pants, these garments are used by young children to facilitate the child's transition from using diapers to wearing regular underpants (i.e., during toilet training). Training pants (and other disposable pull-on pants) have closed sides such that the user or caregiver raises the garment about the user's legs to put it on and slips the garment downward about the user's legs to take it off.

The principal elements of a typical disposable absorbent garment include a liquid permeable inner layer (or topsheet), a liquid impermeable outer layer (or backsheet), and an absorbent core, sandwiched between the inner and outer layers. Elastic members may be incorporated into different parts of the garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and then during wear. In this way, the garment can stretch to accommodate variations in waist size and leg size of the user, while fitting snugly about the waist and legs.

When elastic members are incorporated into a part or area of the garment, that part or area typically becomes a distinct, functional component of the garment. These elastic components include the side panels or ear portions, the waistband, and fastening tabs. The elastic components to which the present invention is directed is generally elongated, and may be a distinct portion of a larger, unitary piece, or a separate, attachable component. Furthermore, the elastic component typically contains one or more sections or layers in addition to the elastic members. In this regard, such an elastic component may be referred to as an elastic composite.

SUMMARY OF THE INVENTION

It is, therefore, one object of the invention to provide an improved disposable absorbent garment, such as a diaper or adult incontinence garment, and further, such a garment incorporating an improved elastic composite as one or more of its components.

For purposes of the present description, the term "elastic band" or "elastic composite" refers to a multi-layer construction of the disposable absorbent garment. In this construction, a plurality of elastic members, such as threads or strands, are disposed adjacent one or more layers, e.g., backsheet and topsheet. In this way, the elastic members imparts elasticity to the adjacent layers and thus, to that part of the disposable absorbent garment. Such an elastic structure may be a distinct attachable component of the garment or may be a distinct portion or section of the garment body or a larger, unitary component of the garment body.

In one aspect of the invention, an elastic composite is provided in a disposable absorbent garment such as a diaper or training pants. The elastic composite has a base layer, a top layer, and an elastic construction disposed therebetween. The elastic construction includes a plurality of spaced apart (e.g. preferably generally equally spaced apart) elastic elements (e.g. strands or threads) that are aligned in generally parallel relation. Further, the top and base layers define a first side edge, a second side edge, and a longitudinal centerline therebetween. The elastic construction is disposed between the two layers and extends in a direction that is between the side edges and is generally parallel with or corresponds to (i.e., overlays) the longitudinal centerline. Further, the elastic elements are oriented along a lateral direction that intersects the side edges and longitudinal centerline (e.g., such that each elastic element is oriented or aligned along a direction that is generally perpendicular to the side edges).

Preferably, the elastic composite includes at least one elasticized region, wherein the elastic construction is disposed, that is spaced inwardly from the side edges and, in some embodiments, positioned generally centrally between the side edges. Such an elastic composite also includes a first non-elasticized region disposed between the first side edge and the elasticized region, and a second non-elasticized region disposed between the second side edge and the elasticized region.

In certain embodiments, the first and second non-elasticized regions provide fastening regions that are generally flat relative to the elastic regions, and may be equipped with a fastening element such as adhesives or a hook or loop element. More preferably, the elastic elements are attached to at least one of the top and base layers such that the elasticized region is shirred when the elastic composite is disposed in a relaxed, un-stretched state. In further embodiments, a second elasticized region is provided between the side edges and a third non-elasticized region is provided between the first and second elasticized regions.

In preferred embodiments, the elastic construction has a centerline extending therethrough that is spaced generally equidistantly from each side edge and the elastic strands are distributed along this centerline and in generally perpendicular relation therewith. Preferably, the direction of this centerline corresponds with a machine direction of the elastic composite band or more specifically, the web material from which the elastic composite band is cut.

In yet another aspect of the invention, a disposable absorbent garment is provided with a topsheet, a backsheet, and an absorbent core disposed between the topsheet and the backsheet and such that a longitudinal centerline of the garment extends through the topsheet, backsheet, and absorbent core. Together, the topsheet, backsheet, and absorbent core provide a central body of the disposable absorbent garment. The inventive garment further includes an elastic composite band that is attached to the central body. The elastic composite band has a first side edge, a second side edge, and a composite centerline extending in between the side edges. The elastic composite band includes a base layer, a top layer, and an elastic construction disposed between the top and base layers and spaced inwardly from each side edge. The elastic construction includes a plurality of spaced apart elastic elements that are distributed in a direction extending between the side edges and each aligned in generally perpendicular relation with the composite centerline.

Preferably, the elastic composite band includes an elasticized region that is positioned generally centrally between the first and second side edges, and wherein the elasticized region is disposed. The elastic composite also has a first non-elasticized region positioned between the first side edge and the elasticized region, and a second non-elasticized region positioned between the second side edge and the elasticized region. In some embodiments, the elastic composite band is attached adjacent an end of the garment leg (e.g., along a waistline) and provides therealong an elastic waistband on the garment. In further embodiments, the garment has two elastic composite bands each attached along a side margin of the garment. In these embodiments, the elastic composite band provides an elastic waist fastening portion of the diaper, such as an elastic side panel or ear portion of the garment or elastic fastening tab. In one particular embodiment, the elastic composite is provided as the central chassis or central body of the garment.

The present invention also relates to a system and a method for making the elastic composite and/or the garment incorporating the elastic composite.

In one aspect of the present invention, a method is provided for making an elastic composite. The elastic composite is made for incorporation into a disposable absorbent garment. The method includes the step of providing an elastic element applicator configured to move a section of a continuous strand of elastic element generally about a plane. A first web of material (e.g., non-woven material) is conveyed in a web moving direction such that the first web intersects the plane. Then, the elastic element applicator is operated to move the elastic element about the plane, thereby applying the section of elastic element onto the first web along a direction generally transverse to the web moving direction. Preferably, the elastic element is applied such that the section of elastic element is retained by the first web and the first web draws the continuous elastic strand from the elastic element applicator as the first web is conveyed away from the plane. More preferably, the elastic element applicator is a spin cylinder or bracket, that is operated to spin the elastic element about the moving first web, thereby applying the elastic element on the first web.

In another aspect of the present invention, another method is provided for making an elastic composite for incorporation into a disposable absorbent garment. The method includes the step of conveying a first web of material and folding each of the side edges of the first web along a side fold line and inwardly toward an inward surface of the first web. This creates a pair of folded flaps adjacent the inward surface and an exposed outward surface having a width defined between the fold lines (i.e., at the folded side edges). A plurality of spaced apart elastic strands is subsequently applied across the width of the exposed outward surface. Then, the applied elastic strands are cut proximate each of the fold lines of the first web (i.e., along the folded side edges), such that the lengths of the elastic strands are generally equal to the width of the outward surface. Thereafter, the folded flaps of the first web are unfolded such that the resulting first web has, applied thereon, a plurality of centrally located elastic strands and non-elasticized side regions defined generally outward of the fold lines. Preferably, the elastic strands are applied in spaced apart, generally parallel relation. Furthermore, the elastic strands are preferably applied by spinning a continuous elastic strand about the first web.

DETAILED DESCRIPTION OF THE INVENTION

Each of FIGS. 1 and 4-9 depict a disposable absorbent garment embodying various aspects of the present invention.

Figure 1:
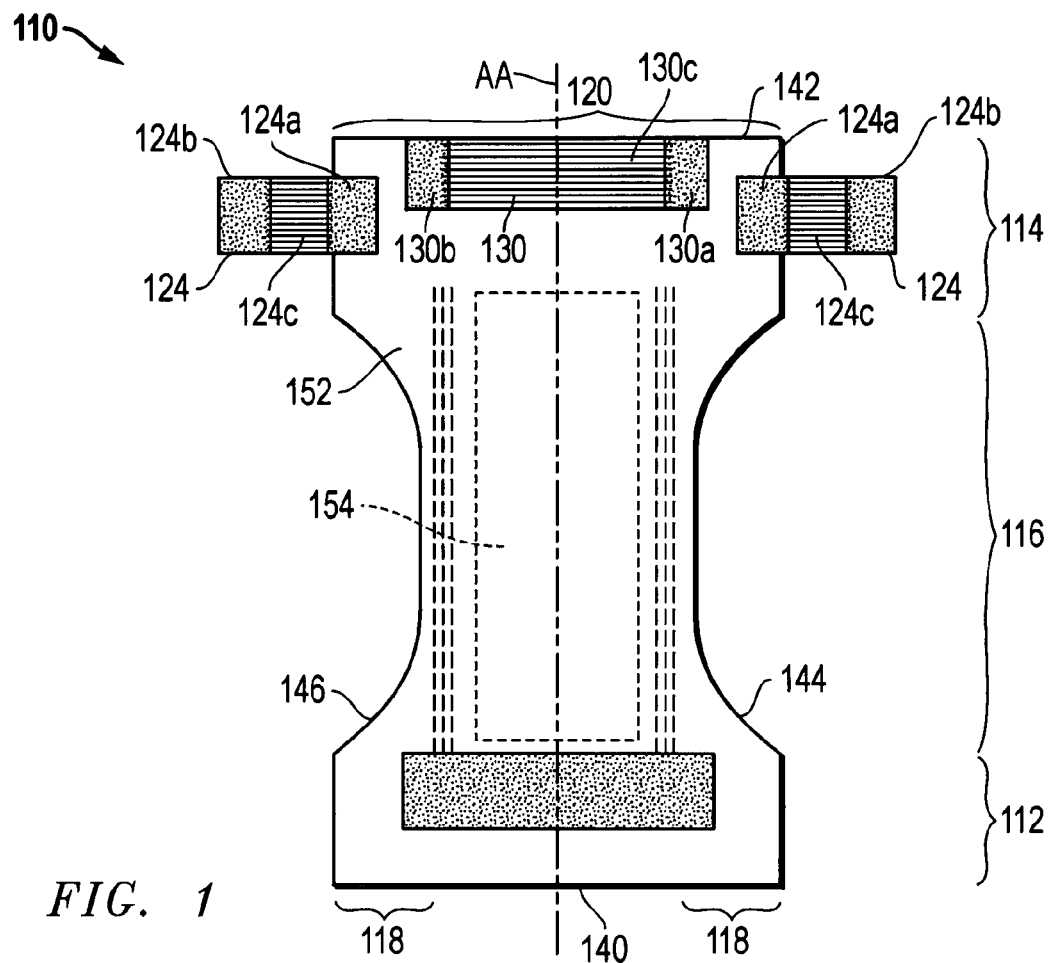
FIG. 1 is a plan view of a disposable absorbent garment in the unfolded configuration; according to the present invention.

More particularly, each of these Figures depict such a garment that incorporates an elastic composite structure or elastic composite in accordance with the present invention. In FIG. 1, a disposable absorbent garment 110 is shown that is suitable for the invention and in the form of a diaper having one or more elastic composites incorporated therein. The elastic composite in FIGS. 1-8 have side and end edges and, thus, may be referred to herein as elastic composite bands. FIGS. 9-16 illustrate a system and process of making the elastic composite (and a garment having the elastic composite) in accordance with the present invention.

The disposable absorbent garment 110 in FIG. 1 is of a type that can be placed against or in proximity to the body of a wearer so as to absorb and to contain various bodily exudates. It should be noted, however, that the present invention is applicable to a variety of disposable absorbent articles and garments, including training pants and a variety of adult incontinence products. As will be described below, the inventive elastic composite or elastic composite band may provide a side panel or ear portion, a waistband, a fastening tab or band, or other distinct elastic component of the garment or article. The inventive elastic composite may also be incorporated into an ear portion to elasticate the ear portion or to supplement the ear portion with an elasticated fastening tab. Accordingly, the present invention is not intended to be limited to the structures and the processes specifically described and illustrated herein. For purposes of description, however, the following discussion will be directed to an exemplary disposable diaper only. Moreover, the invention will be described in the context of its various configurations and aspects. It should be appreciated that alternative arrangements of the inventive disposable absorbent garment and such an elastic composite band may comprise various combinations, which include one or more of the various configurations and aspects of the invention.

FIG. 1 is introduced to illustrate some basic features of a disposable diaper 110, most of which are also applicable to other disposable absorbent garments contemplated by the invention. The diaper 110 includes three main regions aligned along an imaginary longitudinal axis or plane AA. These regions include a first waist region 112 (typically at the front of the user when the garment 110 is worn), a back waist region 114, and a crotch region 116. The diaper 110 is also characterized by a front edge 140, a back longitudinal edge 142, a first lateral or side edge or side margin 144, and a second lateral or side edge or side margin 146.

Along a lateral direction, the diaper 110 includes ear regions or ear portions 118 extending laterally from the waist regions 112, 114. Together, the waist regions 112, 114 and crotch region 116 may be referred to as forming a central body portion 120 of the garment 110 that is positioned within side edges 144, 146. The body portion 120 may also be referred to as being formed by a liquid permeable inner layer or topsheet 152, a liquid impermeable outer layer or backsheet (not shown), and an absorbent core 154 sandwiched between the two layers. The ear portions 118 further include fastening tabs 124 for attaching the waist regions 112, 114 together. The diaper 110 also has an elastic waistband 130 positioned generally along the back edge 142 to facilitate fastening and to enhance the fit and seal of the diaper 110. When the hourglass shaped diaper 110 is worn, the crotch region 116 fits about the crotch of the wearer, and the front and back waist regions 112 and 114, fit about the corresponding waist areas. The ear portions 118, on the other hand, wrap about the wearer and the fastening tabs 124 engage to form a complete, all-around waistline of the diaper 110.

Figure 2A:
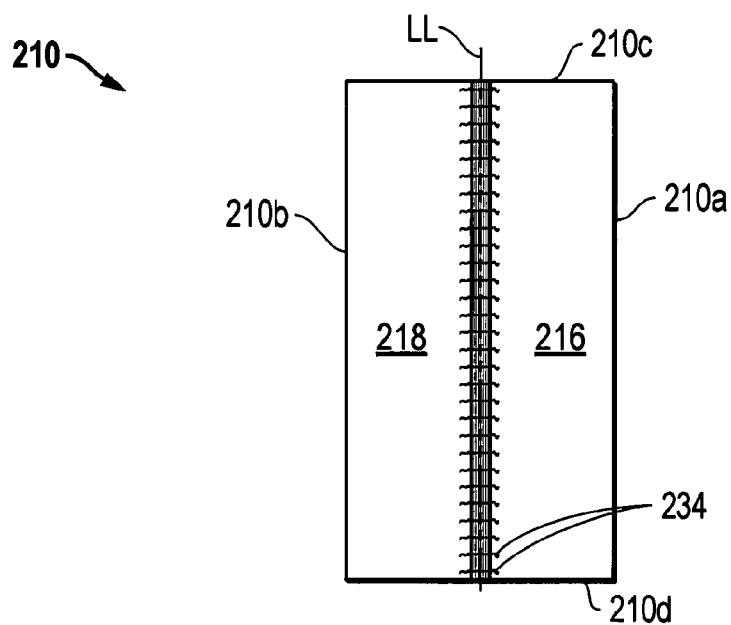
FIG. 2A is a plan view of an elastic composite according to the present invention.
Figure 3:
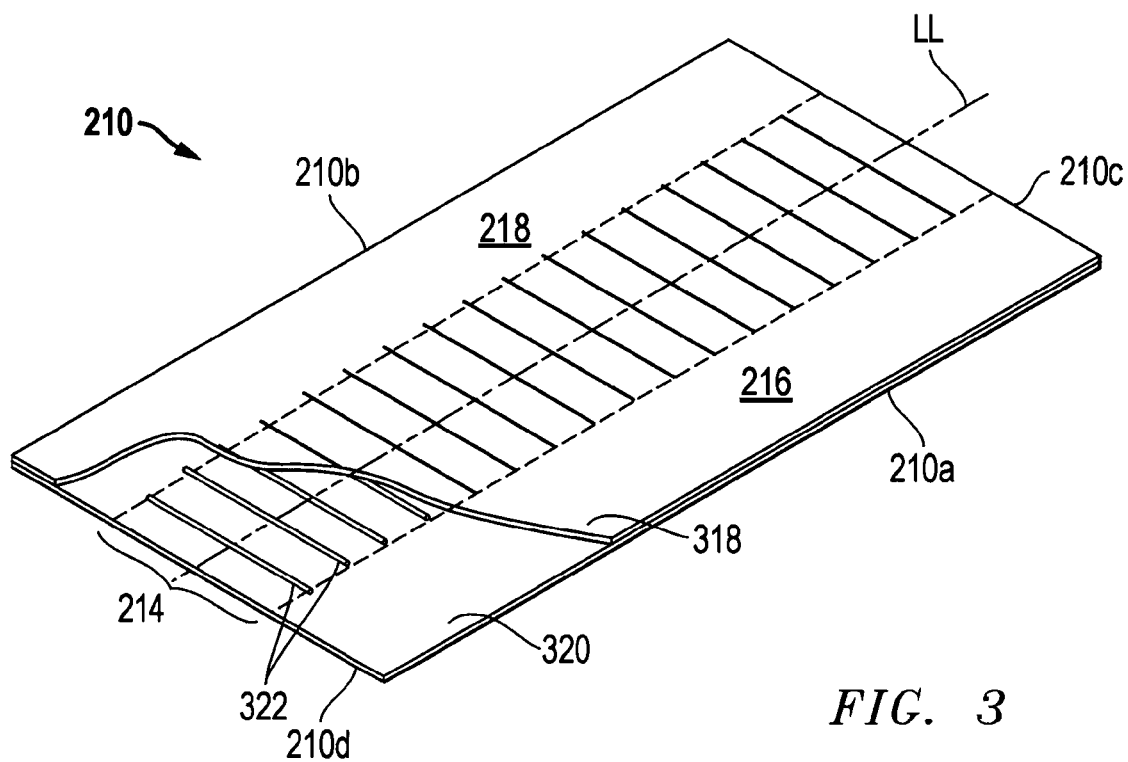
FIG. 3 is a perspective view of the elastic composite of FIG. 2A with a cut-out detail to show an elastic construction.

FIG. 2A depicts a typical elastic composite band 210 according to the invention. More particularly, the elastic composite band 210 is one particularly suited for use as a side panel or fastening tab of a disposable absorbent garment (see, e.g., FIG. 1). FIG. 3 provides a perspective view and partial cut-out of the elastic composite band 210. The elastic composite band 210 may be characterized by an imaginary centerline LL. In one aspect of the invention, the centerline LL preferably corresponds with the machine direction of the elastic composite band 210 during manufacture. The elastic band 210 also has side or longitudinally extending side edges 210a and 210b and laterally extending end edges 210c and 210d. In FIG. 1, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-directional machine direction" or "cross-directional," on the other hand, refers to the direction that is perpendicular to the machine direction. With reference to the elastic composite 20 of FIG. 2, the cross machine direction is the direction XX extending laterally or perpendicularly relative to the longitudinal line LL.

The elastic composite band 210, according to the invention, has a central region 214 in which an elastic construction is situated. Extending laterally from this central elastic or elasticized region 214 are regions 216 and 218, which are substantially non-elasticized. As shown in FIG. 2A, the regions 216, 218 occupy the expanse between the central elastic region 214 and the side edges 210a, 210b. Now with reference to FIG. 3, the elastic composite band 210 has a top layer 318 and a bottom or base layer 320. The two layers 318, 320 preferably extend the total width and length of the elastic composite band 210, thereby providing the side edges 210a, 210b, and the end edges 210c, 210d. Both the base layer 320 and the top layer 318 are preferably a non-woven, breathable, disposable material such as propylene, non-woven fabric, breathable polyethylene/polypropylene films, or non-porous films (or combinations of these materials). The base layer 320 and top layer 318 adhere to one another, thereby sandwiching and securing a plurality of elastic strands 322 therebetween.

The elastic strands 322 may be substituted, in alternative embodiments, by suitable elastic elements such as elastic strands, threads, ribbons, and elastic glue beads. In one aspect of the invention, the elastic elements or strands 322 are distributed along a direction that extend between the side edges 210a, 210b and parallel with (or corresponding to) center line LL. Further, each elastic element 322 is generally aligned or oriented in a direction corresponding with the lateral or cross-machine direction, i.e., in a direction generally perpendicular to the longitudinal center line LL and intersecting the side edges 210a, 210b. Preferably, the strands 322 are disposed in generally parallel relation and spaced apart generally equally along the longitudinal direction. More preferably, the elastic strands 322 are of generally equal length. Accordingly, when the elastic composite band 210 is worn, the strands 322 impart elasticity into the structure which allows the band 210 to stretch in the lateral or cross-machine direction XX.

Figure 2B:
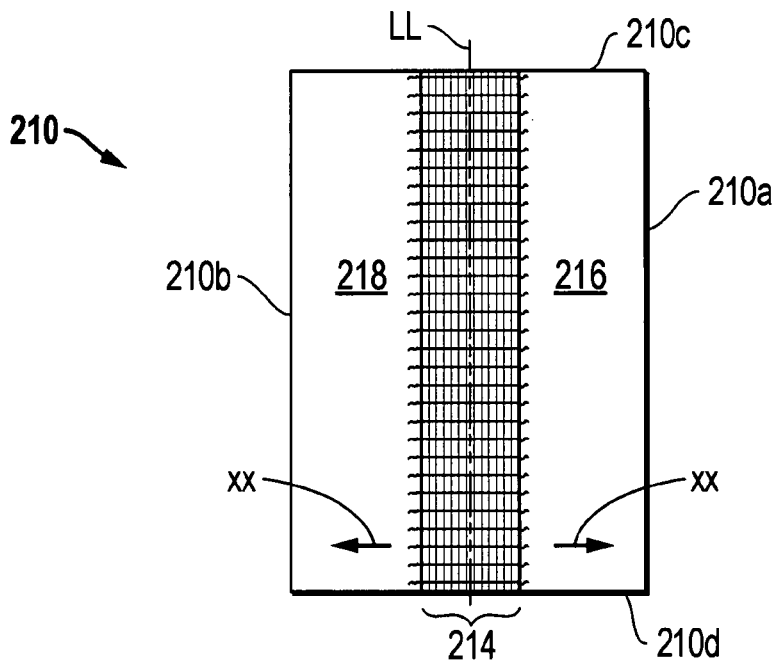
FIG. 2B is a plan view of the elastic composite of FIG. 2A shown in an extended, stretchable condition.

The elastic strands 322 are preferably tensioned during securement between the top and base layers 318, 320. FIG. 2B illustrates the elastic composite band 210 in a laterally stretched condition. In this condition, the central elastic region 214 has a width that is almost equal to the non-elasticized zones 216 and 218. When returned to the non-laterally stretched or relaxed condition, as shown in FIG. 2A, the central elastic region 214 contracts and crimps to a substantially reduced width. In this condition or state, the contracted elastic strands 322 shirrs the elastic composite 210 and provide pleats 234 in the contracted elastic region 214.

The elastic composite band 210 may originate from a web of material that is wound onto spools or festooned. Typically, the user of such material will cut the material to a length required of a particular application. In some applications, one such web of material may provide the source of multiple components of the inventive disposable absorbent garment.

Returning to FIG. 1, the inventive disposable absorbent garment 110 employs one or more elastic composite bands according to the invention, as described above. The disposable absorbent garment 110 employs in each of the ear portions 118, a fastening tab 124 having the inventive elastic composite construction. As the fastening tab 124, the elastic composite band is configured such that one non-elasticized region 124a is attached to and overlaps the central body 120 of the garment 110 while a second non-elasticized region 124b is situated outboard of the side margins 144, 146. An elasticized region 124c, as shown in FIG. 1, provides elasticity, and thus, stretch in the lateral or cross-machine direction (of the elastic composite). In respect to the rest of the garment 110, the elasticity or stretch provided by the central elastic region 124c directed along a direction that is generally perpendicular to the longitudinal center line AA of the garment 110, and corresponds with a direction that wraps about the waistline of the user.

The disposable absorbent garment 110 in FIG. 1 also provides an elastic composite, according to the invention, as the waistband 130. The waistband 130 is situated centrally in the waist region 114. Further, the elastic composite waistband 130 is disposed such that non-elasticized regions 130a, 130b are positioned outwardly of the longitudinal line AA of the garment 110, while an elasticized region 130c is positioned centrally across the longitudinal center line AA. Moreover, the elasticized region 130c is configured such that the elastic strands are aligned or oriented in a direction that is generally perpendicular to the longitudinal center line AA. In this way, the elastic composite waistband 130 imparts elasticity about the waist region 114 of the garment 110, and in a direction corresponding with the direction of waistline about the user.

Figure 4:
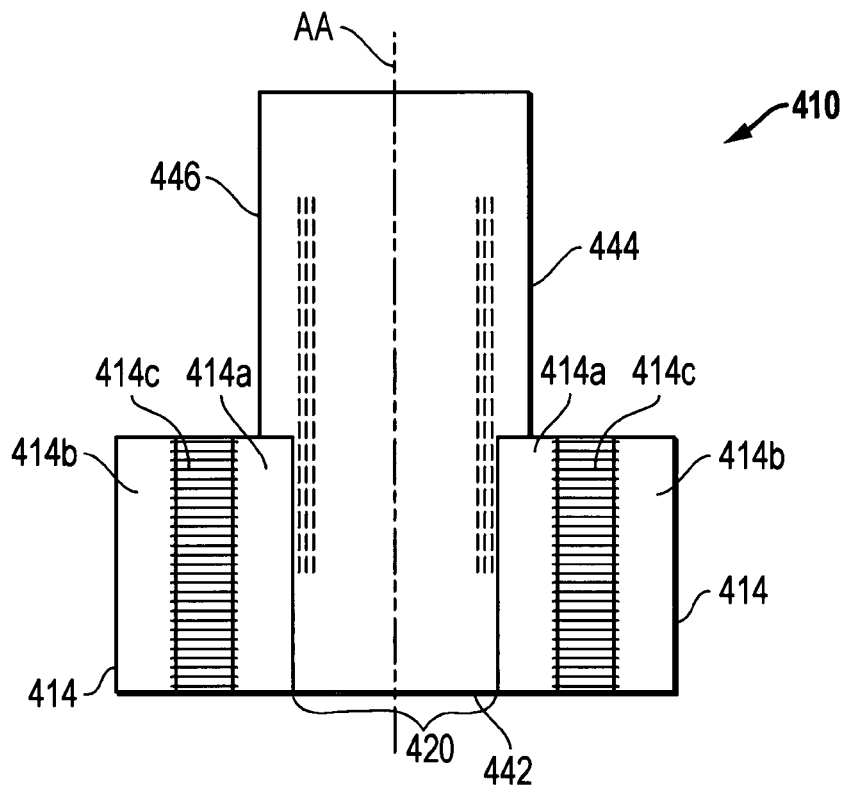
FIG. 4 is a plan view of an alternative disposable absorbent garment according to the invention.

FIG. 4 depicts an alternative disposable absorbent garment 410 according to the invention. Specifically, FIG. 4 depicts a disposable absorbent garment 410 employing elastic composites according to the invention as attachable ear portions or side panels 414. The elastic composite side panels 414 are separate components that are attached to a central body 420 of the garment 410. The elastic composite side panels (or ear portions) 414 are attached near one waist edge 442 of the garment 410 and such that the centerline AA of the side panel 414 is generally parallel with the longitudinal centerline AA of the garment 410. Moreover, each of the elastic composite side panels 414 has a non-elasticized region 414a that is positioned outboard of the side margins 446 of the garment 410 and a second non-elasticized region 414b that is attached inboard of the side margin 446 (or side margin 444). Thus, a central elastic region 414c is situated outboard of the side margin 446 and not directly attached thereto. When the garment 410 is in use, the central elasticized region 414a allows the side panel to stretch in a lateral or cross-machine direction that corresponds with the lateral direction relative to the longitudinal centerline AA of the garment 410. Accordingly, when the garment 410 is worn, the elastic side panel 414 allows for stretching about the waistline of the user.

Figure 5:
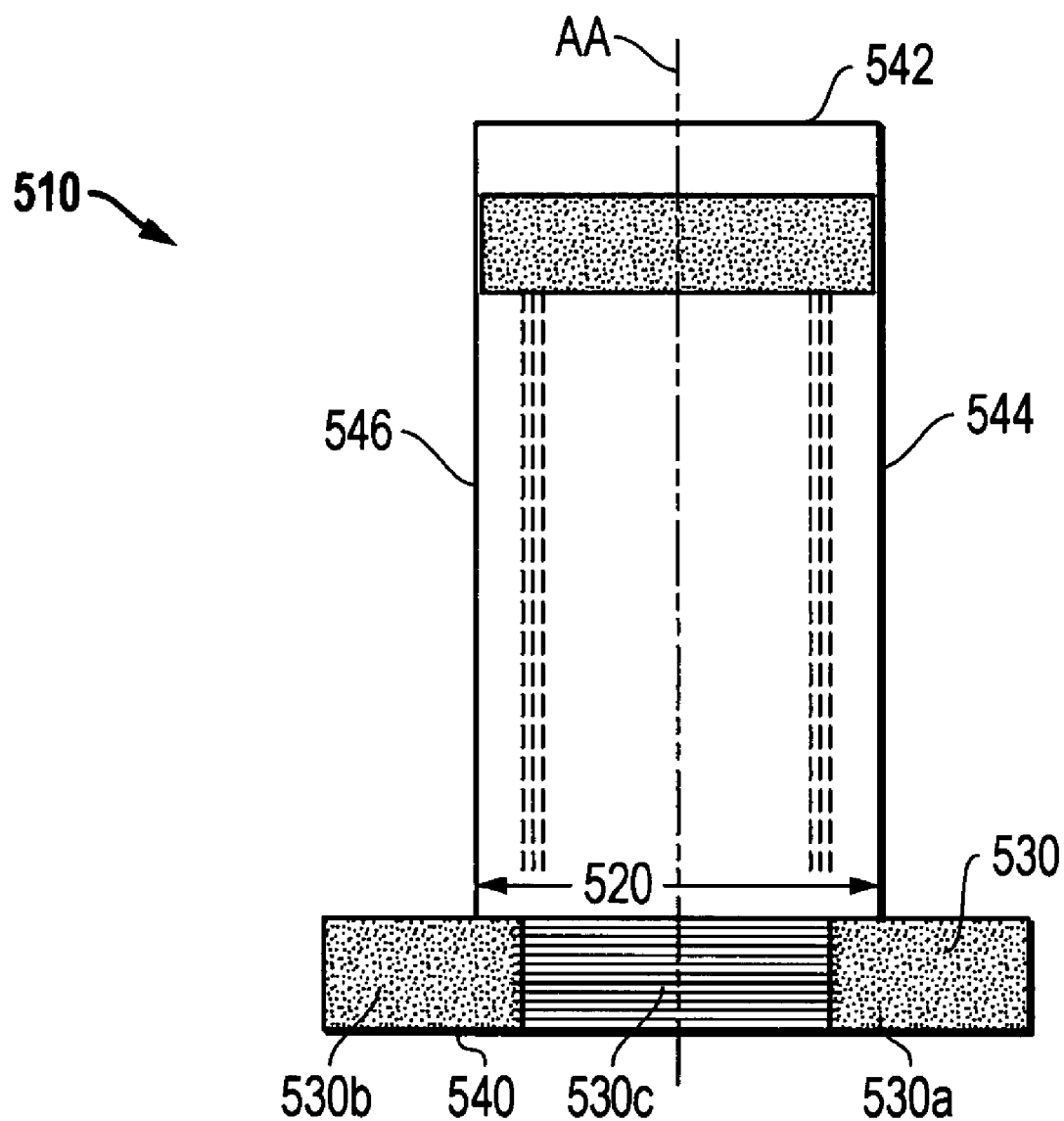
FIG. 5 is a plan view of another alternative disposable absorbent garment, according to the invention, incorporating an elastic composite as a waistband.

FIG. 5 depicts yet another alternative embodiment of a disposable absorbent garment 510 according to the invention. The disposable absorbent garment 510 is a diaper partially defined by end or waist edges 540, 542 (not shown) and side margins 544, 546. Further, the inventive disposable garment 510 has a central body 520 and a separate, attachable elastic waistband 530. Similar to the garments 110, 410 in FIGS. 1 and 4, respectively, the garment 510 employs an elastic composite, as the elastic waistband 530. The inventive elastic waistband 530 is attached adjacent a waist edge 542 of the garment 510 and is positioned centrally about the longitudinal centerline AA. The elastic composite waistband 530 is situated such that non-elasticized regions 530a, 530c extend laterally past the side margins 544, 546, respectively. The central elasticized region 530c is positioned centrally within the central body 520 and side margins 544, 546. The elastic strands of the central elastic region 530c is further situated such that the elastic region 530c provides elasticity or stretch in a lateral direction relative to longitudinal centerline AA. Again, in this way, the elastic composite waistband 530 according to the invention allows for the garment to fit snugly and effectively about the waistline of the user.

Figure 6:
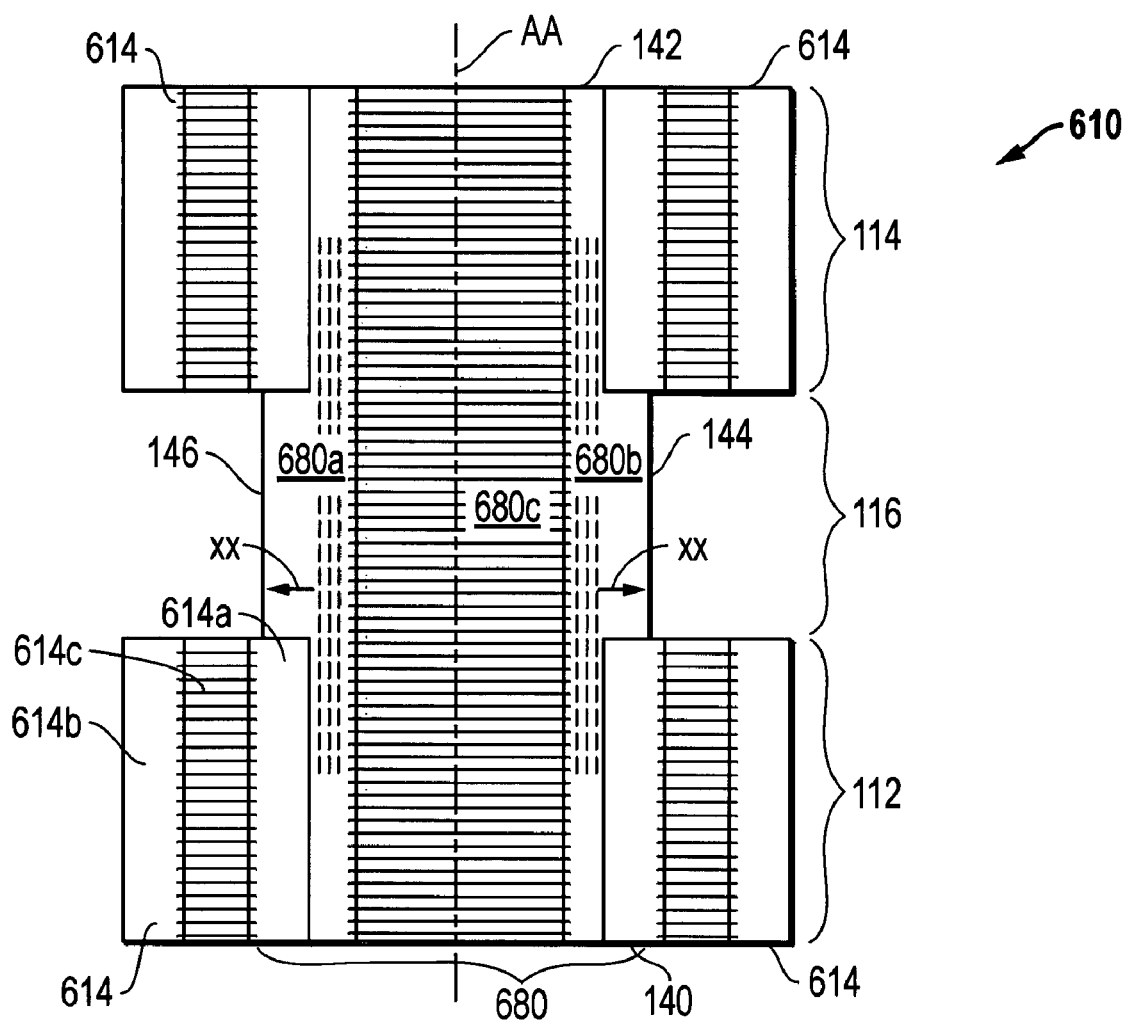
FIG. 6 is a plan view of yet another alternative disposable absorbent garment, according to the invention, further incorporating an elastic composite as a central body chassis.

FIG. 6 illustrates an alternative disposable absorbent garment 610, according to the invention (wherein like reference numerals are used to indicated like elements), in which the inventive elastic composite band is incorporated into various areas or as various garment components. The garment 610 has a front waist region 112, a back waist region 114, and a crotch region 116 positioned therebetween. As with the garment 410 of FIG. 4, an elasticized composite band 614 is attached to each side margin 144, 146, near end edge 140, as an elasticized side panel 614. A second pair of elastic composite bands is attached as an elasticized side panel 660 along the opposite end edge 42 of the garment 610.

FIG. 6 also illustrates the use of the inventive elastic composite band to provide an elasticized central body or chassis 680 at or beneath the crotch region 116 of the garment 610 and in support of an absorbent core (not shown so as to clearly display the chassis 680). The absorbent core is preferably adhered to and movable with the elasticized chassis 680. Thus, the core is preferably a conformable (changes shape in accordance with an outside force), elastic, or extensible (e.g., pulled and permanently stretched) body, as is generally known in the art. In this way, the main or central body of the garment 610 is elasticized in a lateral direction XX that is generally perpendicular to a longitudinal centerline AA of the garment 610. In the garment 610 of FIG. 6, the inventive composite band provides the entire length of the central body or chassis 680. The elastic composite chassis 680 has an elasticized region 680c situated between two non-elasticized regions 680a, 680b. Preferably, the elasticized region 680c provides an elastic construction of a plurality of elastic strands as disclosed previously in respect to the embodiments of FIGS. 1-5. In the illustrated embodiment, the elasticized region 680c extends between end edges 140, 142, thereby imparting lateral elasticity (stretchability) across the entire garment length.

Figure 4A:
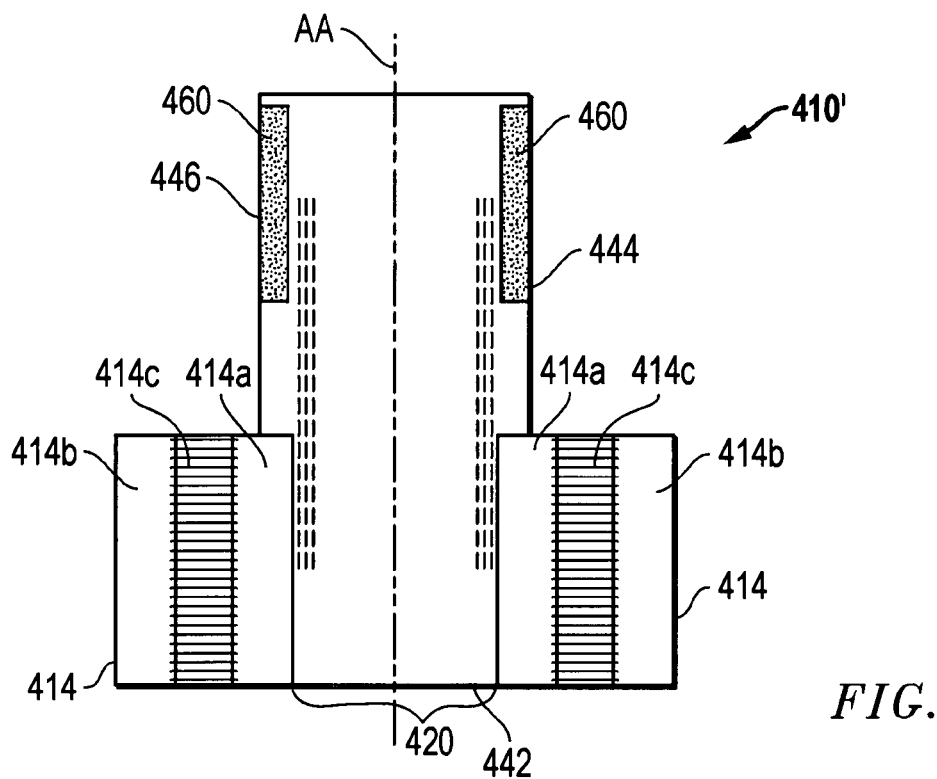
FIG. 4A is a plan view of a convertible or converted disposable absorbent garment according to the invention.

Now turning to FIG. 4A, the disposable absorbent garment 410' is provided with fastening means 460 along the margins 444, 446, and near one end opposite of the elastic composite side panels 414. Provision of the fastening means 460 allows for fastening of the ends of the garment. Accordingly, this particular garment 410 is referred to as a convertible or converted garment, in that it allows the garment to be used as a diaper and alternatively, as a training pants type garment.

The fastening means 460 may be provided with fastening elements such as hooks or loops which can correspondingly adhere or attach to the non-elasticized zones 414a, 414b of the side panels 414. The garment 410' may come with the fastening means 460 attached with the side panels 414, in the way of a training pant. Furthermore, the fasteners 460 may be detached from the side panel 414, in the way of a diaper.

Figure 6A:
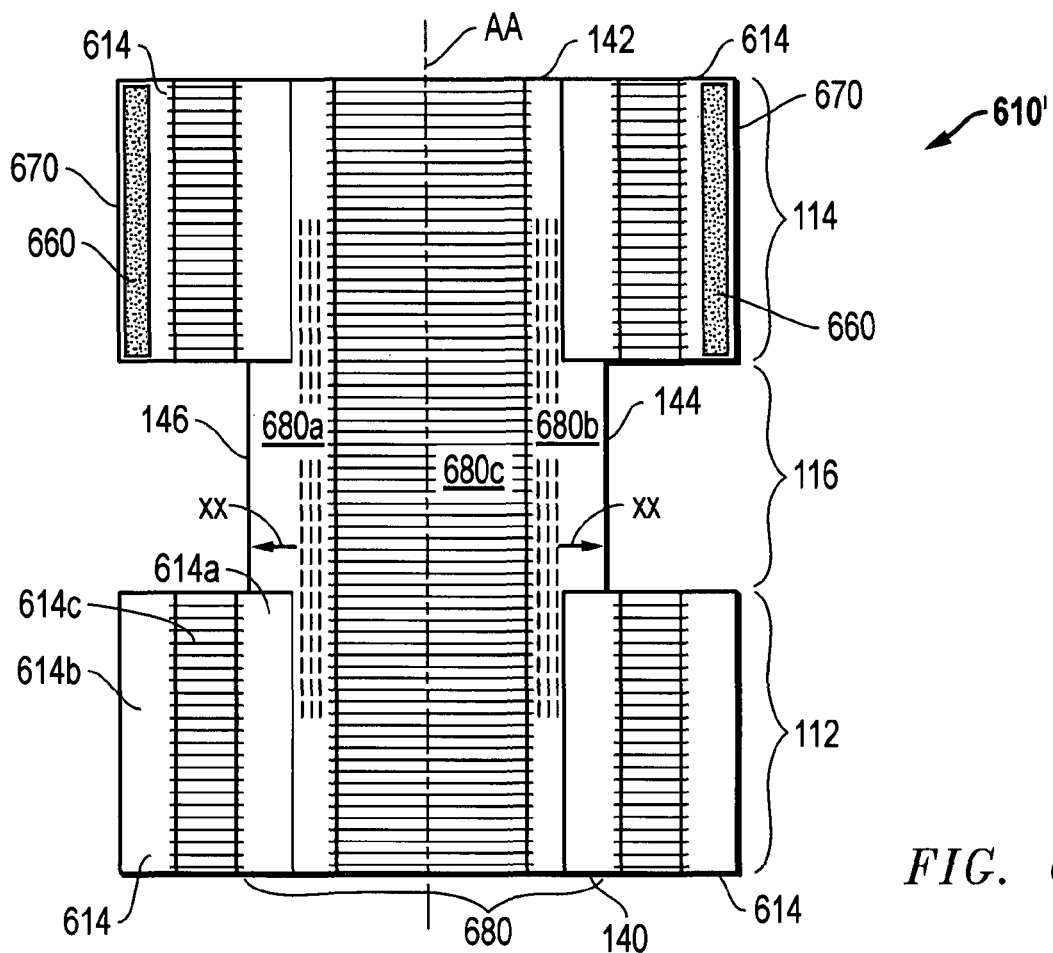
FIG. 6A is a plan view of a convertible or converted disposable absorbent garment according to the invention.

Now turning to FIG. 6A, the disposable absorbent garment 610' is also provided with fastening means 660 on the elastic composite side panel 614. The fastening means 660 may include fastening elements such as hooks or loops, which can adhere and attach to the non-elasticized zone 614a, 614b of corresponding side panel 614.

Figure 7:
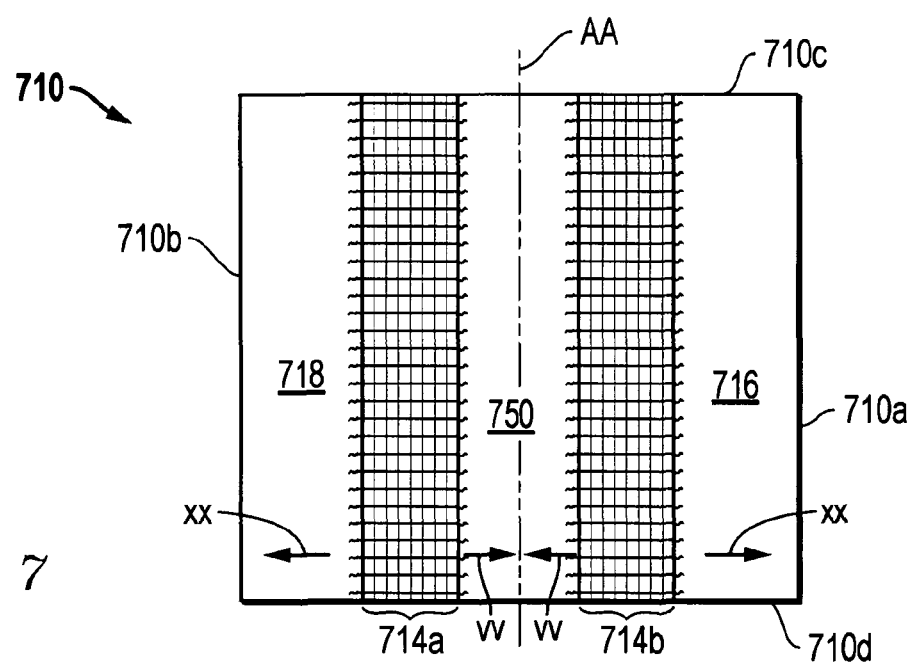
FIG. 7 is a plan view of an alternative elastic composite according to the present invention.

FIG. 7 depicts an alternative embodiment of an elastic composite band according to the present invention. The elastic composite band 710 illustrated therein differs from the previously described elastic composite band (see e.g. FIGS. 2 and 2a) in that the elastic composite band 710 includes two elasticized regions 714a and 714b. The elasticized region 714a, 714b are preferably equidistantly spaced apart on either side of the longitudinal centerline AA. The spacing of the elasticized regions 714a, 714b creates right and left non-elasticized or dead regions 716, 718, as well as central non-elasticized region 750. The elasticized regions 714a, 714b imparts elasticity to elastic composite band 710a in the lateral directions XX, and in the central non-elasticized region 750, also in the opposite lateral direction VV.

Figure 8:
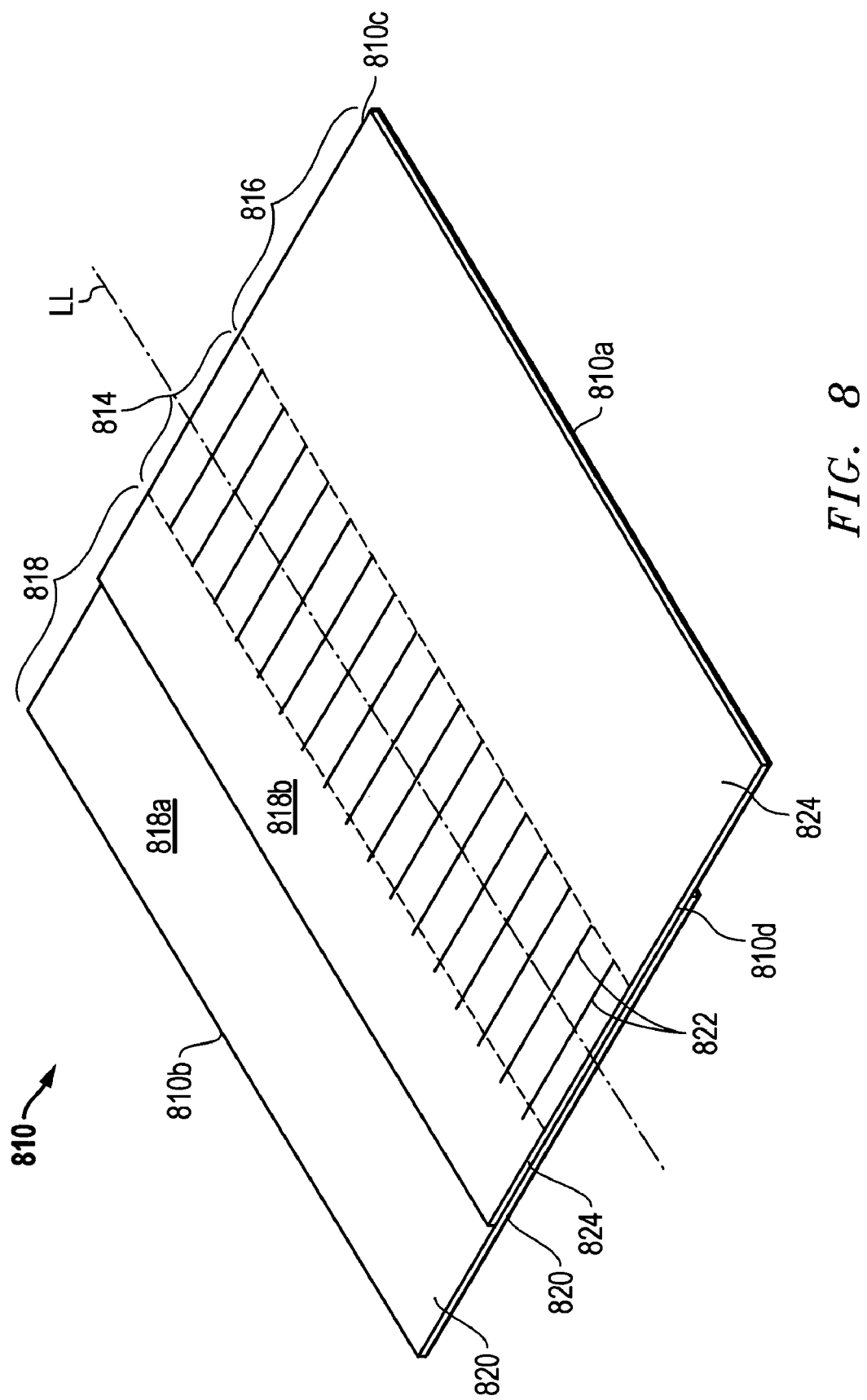
FIG. 8 is a perspective view of yet another alternative elastic composite according to the invention.

FIG. 8 depicts yet another embodiment of an elastic composite band 810 according to the invention. The inventive elastic composite band 810 has, as in previously described embodiments, a central elastic or elasticized region 814 and regions 816 and 818 that are substantially nonelasticized and extend laterally from the central elasticized region 814. The elasticized region 814 is again comprised of a plurality of elastic strands 322 that are disposed in generally parallel relation, and generally perpendicular with a longitudinal centerline LL of the elastic composite band 810 (and the elasticized region 814). The elastic composite band 810 also has end side edges 810a, 810b, and end edges 810c, 810d.

In yet another aspect of the invention, the elastic composite band 810 is further comprised of base layer 820 and top layer 824. As shown in FIG. 8, base and top layers 820, 824 sandwich the elastic strands 822 therebetween. In contrast to previously described embodiments, layers 820 and 824 are offset in respect to one another. Specifically, the two layers 820, 824 are not positioned squarely or evenly one atop another, but overlap. In this way, the elastic composite band 810 is made wider. In particular, by offsetting the two layers 820, 824, the nonelasticized regions 816, 818 are extended and may be referred to as having an outside section (e.g., 818a) formed by one of the layers 820, 824 and an inside section (e.g., 818b) having both a top and a bottom layer 820, 824. Preferably, the two layers 820, 824 are two plies of nonwoven material. The wider nonelasticized, nonwoven regions 816, 818 provide a working area on which fastening materials and other accessories or structural attributes of the disposable absorbent garment may be situated. In various embodiments, the offset or overlap of the two layers 820, 824 may be varied so as to create nonelasticized regions 816, 818 of various widths. Moreover, a wider elastic composite band (and specifically, nonelasticized regions of the elastic composite band) is attained, without increasing the size of the nonwoven layers.

Figure 8A:
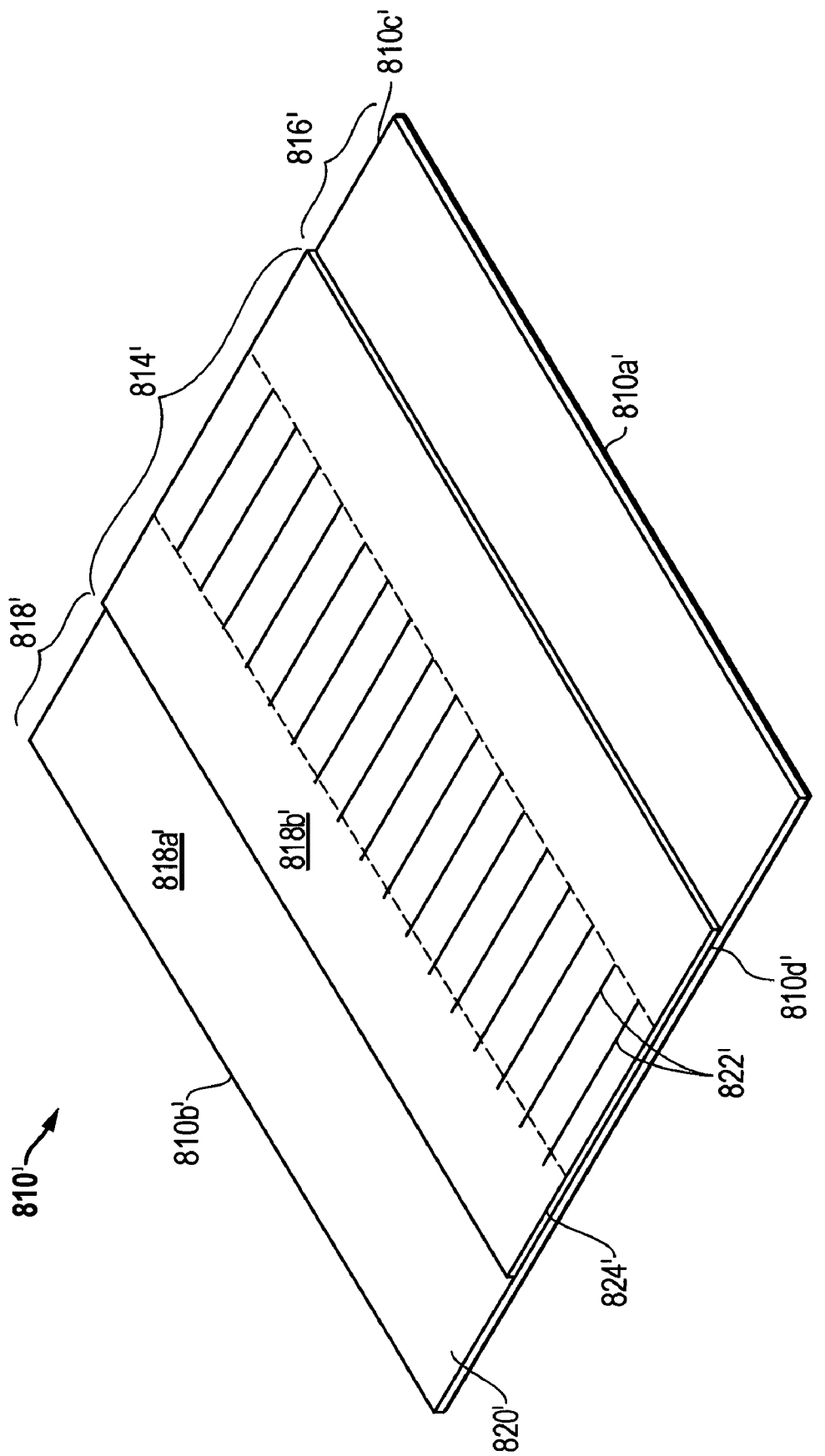
FIG. 8A is a perspective view of yet another alternative elastic composite according to the invention.

FIG. 8A illustrates a further variation of the elastic composite band 810 in FIG. 8, in accordance with the present invention. Specifically, FIG. 8 depicts an inventive elastic composite band 810' having a central elastic or elasticized region 814' and regions 816' and 818' that are substantially nonelasticized ("dead zones") and extend laterally from the central elasticized region 814'. The elasticized region 814' is again comprises of a plurality of elastic strands 822' that are disposed in generally parallel relation and generally perpendicular with a longitudinal centerline LL of the elastic composite band 810' (and the elasticized region 814').

In this particular embodiment of the invention, the elastic composite band 810' includes a base layer 820' and a top layer 824' that is significantly narrower than the base layer 820'. The base and top layers 820' and 824' sandwich the elastic strands 822' therebetween. Preferably, the width of the top layer 824' is no less than 5 mm wider than the width of the central elasticized region 814'. This design further illustrates yet another aspect of the invention, and a manufacturing process, which results in a reduction of the raw material costs of the disposable absorbent garment, and more specifically, the elastic composite band 810'.

Figure 9A:
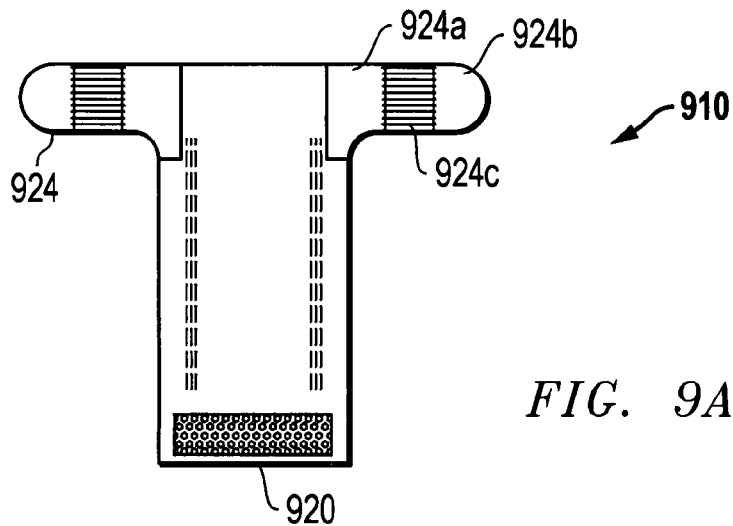
FIGS. 9A-9C are plan view of a further alternative disposable absorbent garments, according to the invention.
Figure 9B:
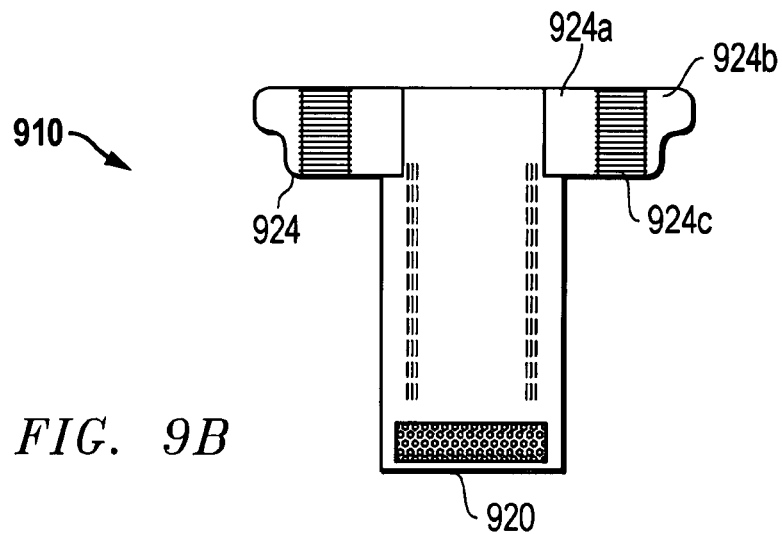
Figure 9C:
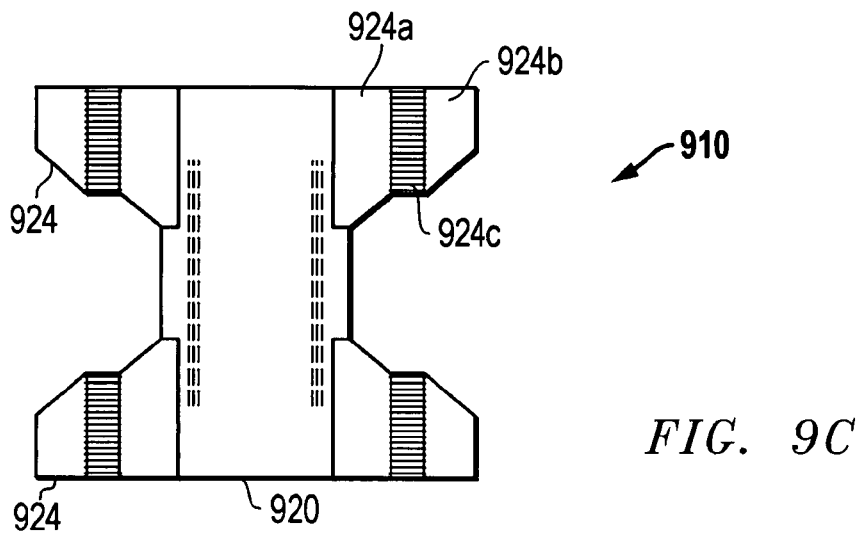

FIGS. 9A-9C are provided to illustrate further embodiments of the present invention. More specifically, FIGS. 9A-9C provide alternate designs, specifically alternate shapes, of the inventive elastic composite band. In these figures, like elements are referenced using like numerals.

Referring to FIGS. 9A and 9B, a disposable absorbent garment 910 is shown having a central body 920 and elastic composite bands in the form of ears or side panels 924. The ears 924 have inner and outer nonelasticized regions 924a, 924b, and a central elasticized region 924c situated therebetween. These two figures illustrate an elastic composite band according to the invention having nonelasticized regions 924a and 924b that are different from one another and do not provide side edges of the elastic composite band 924 which are in generally parallel relation. In both designs, the side edge of the outer nonelasticized regions 924b are rounded or curved. The shape of the elastic composite bands 924 in these two figures provide, among other advantages, a more attractive product as perceived by the consumer.

Now turning to FIG. 9c, yet another variation of the elastic composite band 924 is shown applied to a training pants 910. Specifically, the inventive elastic composite band 924 has nonelasticized regions 924a and 924b of different geometries. This design of the elastic composite bands 924 provide an aesthetic as well as a functional advantage. The functional advantage comes in the form of an improved fit around the wearer's leg, particularly due to the shape of the elastic composite band 924.

FIGS. 10-16 depict a system and system components, and illustrate a method or process of making or manufacturing the elastic composite according to one embodiment of the invention. In one aspect of the inventive process, two elastic composite web outputs 1031 are produced from four separate non-woven web inputs 1003a, 1003b, 1003c, and 1003d. To facilitate the description of the present invention, reference may be made to U.S. Pat. Nos. 3,627,621 and 2,902,395, each of which discloses certain features of the prior art system and process for manufacturing a lamination and/or composite having non-woven materials. Each of these patents is hereby incorporated by reference and made a part of the present disclosure. In particular, reference may be made to certain basic components of a system or apparatus for manipulating non-woven materials and fibers.

Figure 10:
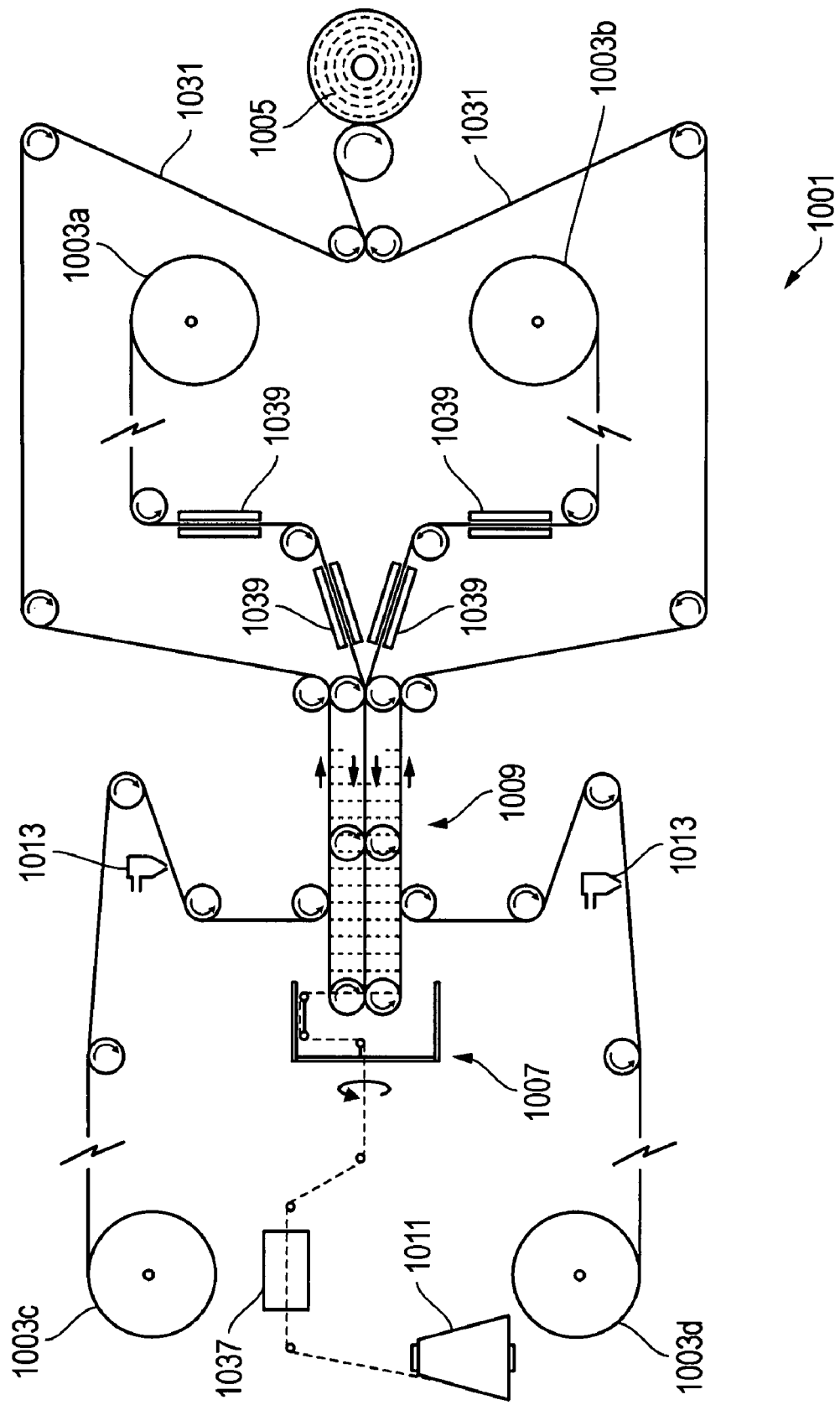
FIG. 10 is a simplified schematic of a system for manufacturing the elastic composite according to the present invention.

Referring first to FIG. 10, a system 1001, according to the invention, includes four separate non-woven web inputs 1003a-1003d, which provide a web or roll of non-woven material for the elastic composite. The system further includes an output assembly or reel 1005 that receives two elastic composite webs 1031 from the rest of the process.

These two separate elastic webs may be fixed together to produce the kind of composite described in respect to FIG. 7 (or maintained separately).

Central to the inventive system 1001 are a conveyor assembly 1009 for receiving, manipulating, and conveying each of the non-woven web inputs. The conveyor assembly 1009 is positioned and operatively associated with an elastic element applicator such as a spinning head assembly 1007, that applies elastic fibers or strands upon, onto, and or integrally with the non-woven web inputs. The spinning head assembly 1007 further includes a spin head 1017, preferably in the form of a spinning bracket, or cylinder 1017 and the like. The spin cylinder 1017 is configured to hold an "end section" of the continuous strand WW of elastic and move it about a generally vertical plane XX in a reciprocal or repetitive pattern (relative to the conveyor assembly 1009). This plane XX is defined by the area within the spinning perimeter of the cylinder 1017 and which is traced by the outer most bracket or eye 1017*b* securing the strand of elastic WW to the spin cylinder 1017. The paths of the spinning head 1017 and the section of elastic strand retained thereby are provided on the plane XX.

As shown in the schematic of FIG. 10, nonwoven inputs 1003*a* and 1003*b* are fed, utilizing a series of rollers, into the conveyor assembly 1009. Before the two nonwoven webs are fed into the conveyor assembly 1009, the webs are directed through the folding guides or plates 1039. The folding guides 1039 serve to effectively reduce the overall width of the nonwoven web by folding the lateral or side edges along a pre-determined, longitudinally-extending side fold line YY. The first folding guide 1039*a* initiates the first 90° turn while the second folding guide 1039*b* initiates a second 90° turn. The roller 1039 disposed in between the guide 1039*a*, 1039*b* facilitates the folding process. The two folding guides 1039 and roller 1369 may be referred together as a folding guide assembly.

Figure 16:
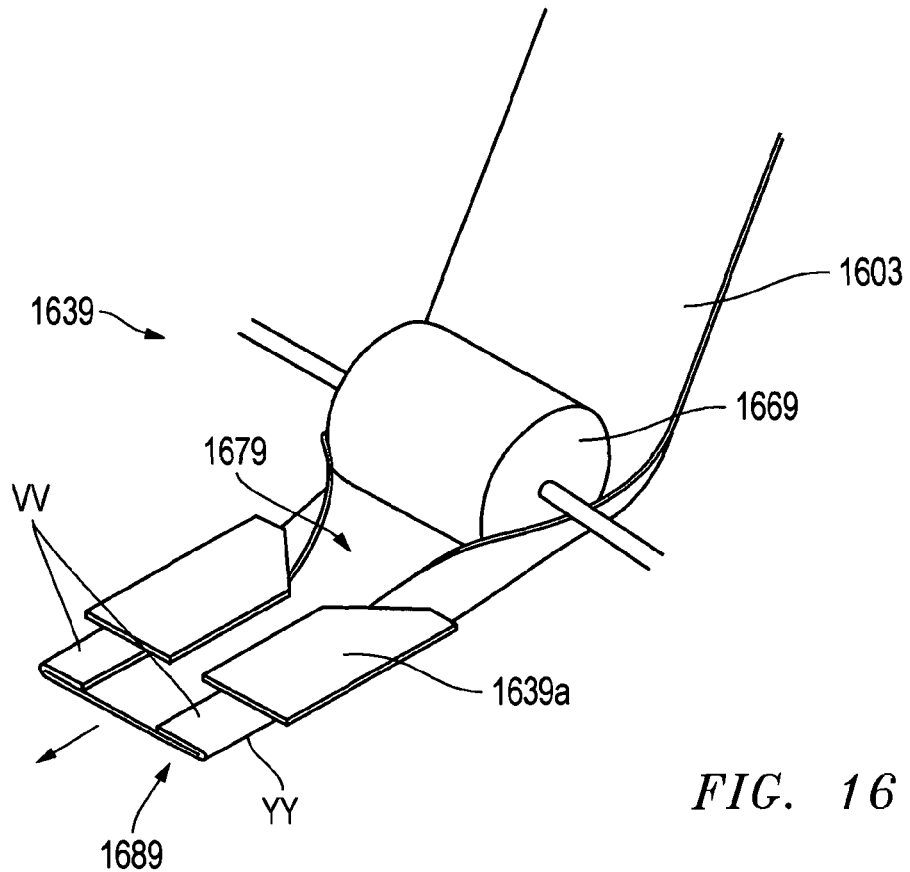
FIG. 16 is a simplified illustration of a folding guide assembly for use with the system and method according to the invention.

FIG. 16 illustrates yet another typical folding guide assembly. The folding assembly 1639 includes folding plates 1639 and a roller 1669 upstream of the folding plates 1639. A web 1603 is passed around the narrow roller 1669, whereby the width of roller 1669 helps determine the width of the web 1603 between the folded flaps VV (i.e., the width of exposed outward surface 1689 defined between the fold lines YY). The width of the roller 1669 is substantially less than the width of the nonwoven web 1603. As a result, the edges of the non-woven web 1603 list and curl up around the sides of the roller 1669, thereby initiating the folding process. The flat plates 1639 then helps to complete the fold and hold the folded sides down. Another folding guide (not shown) may be provided in a position upstream of the folding roller 1669 to help guide or initiate the folding process.

For purposed of the present Description, the inward surface 1679 is the surface or side of the web 1603 toward which the folded flaps VV are turned. The exposed outward surface 1689 is the surface opposite of the inward surface 1679.

The conveyor assembly 1009 is set up so as to guide these two nonwoven webs 1003*a* and 1003*b* through the center of the assembly 1009 towards and eventually inside the elastic spin cylinder 1007 (into the spinning path). Once inside the spin cylinder 1017 the conveyor assembly 1009 delivers the nonwoven webs to each outside, upper and lower faces (outward faces) of the conveyor assembly 1009. At this point the direction of travel of the nonwoven webs are reversed and the webs are directed out of the spin cylinder 1007. As the nonwoven webs exit the spin cylinder 1017, an elastic strand WW is wrapped around the entire conveyor assembly 1009, and as it contacts the upper and lower face of the web platforms it comes into contact with the nonwoven web. As shown in several of the Figures, the elastic strand WW is applied crosswise or laterally on the web, and transverse to the direction of the moving web. The friction between the tensioned elastic strand and the nonwoven webs on the upper and lower faces of the conveyor assembly draws the "wrapped" elastic strand out of the spin cylinder 1017 and towards contact with two further nonwoven webs 1003*c* and 1003*d*.

The nonwoven webs 1003*c* and 1003*d* are operatively positioned upstream of an adhesive applicator 1013. Utilizing a system of rollers in conjunction therewith, the non-woven inputs 1003*c*, 1003*d* and adhesive applicators 1013 apply a web of pre-glued non-woven material onto the conveyor assembly 1009 and onto the elastic strand "wrapped" around the nonwoven webs 1003*a* and 1003*b*.

Furthermore, the system 1001 employs a standard elastic input source, e.g., a bobbin of elastic yarn, that feeds elastic strands or fibers WW onto a tensioning/speed controlling unit 1037 and then to the spin cylinder or the spinning head 1017, so as to apply the strands WW onto the conveyor assembly 1009 and the non-woven material webs conveyed therethrough. Elastic is taken off the bobbin, box or positive drive system and fed through a tension and speed controlling motor towards the spin cylinder 1017. The elastic WW is delivered through a hollow shaft in the motor controlling the spin cylinder 1017. The elastic WW then passes into the spin cylinder 1017 and is guided by rollers, eyes or any other suitable mechanism around the inside face of the spin cylinder 1017.

In alternative embodiments of the invention, the above components may be positioned differently in respect to one another, and may employ other standard components not discussed herein. Moreover, the system and process illustrated may be readily integrated into or with one of several known systems and processes for manufacturing disposable absorbent articles and garments. Such integration will be apparent to one skilled in the relevant consumer product or other relevant art, upon reading and viewing the present disclosure.

Figure 11:
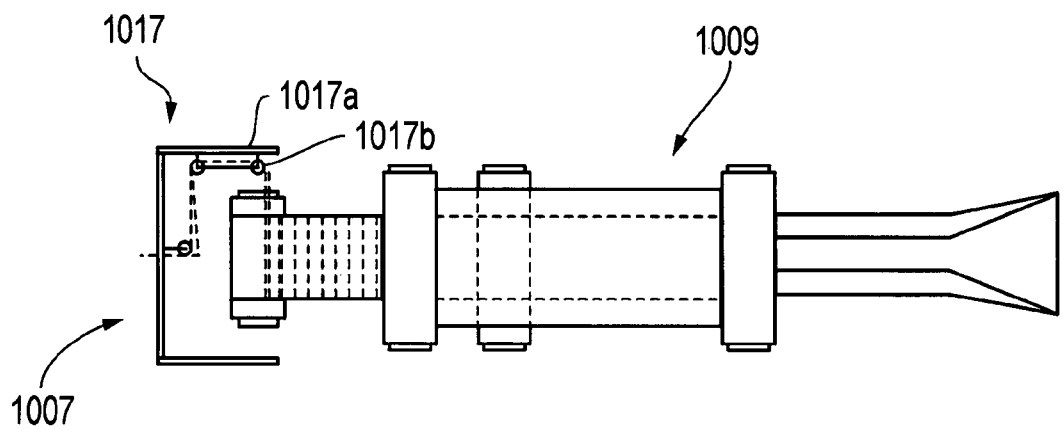
FIG. 11 is a top view of an elastic element applicator assembly for use with the system of FIG. 10.
Figure 12:
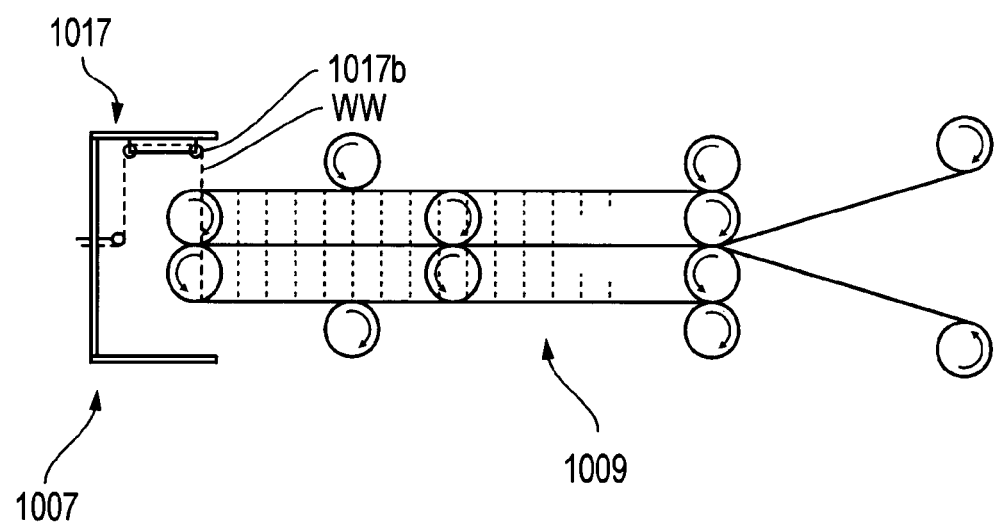
FIG. 12 is a side view of the assembly of FIG. 11.
Figure 13:
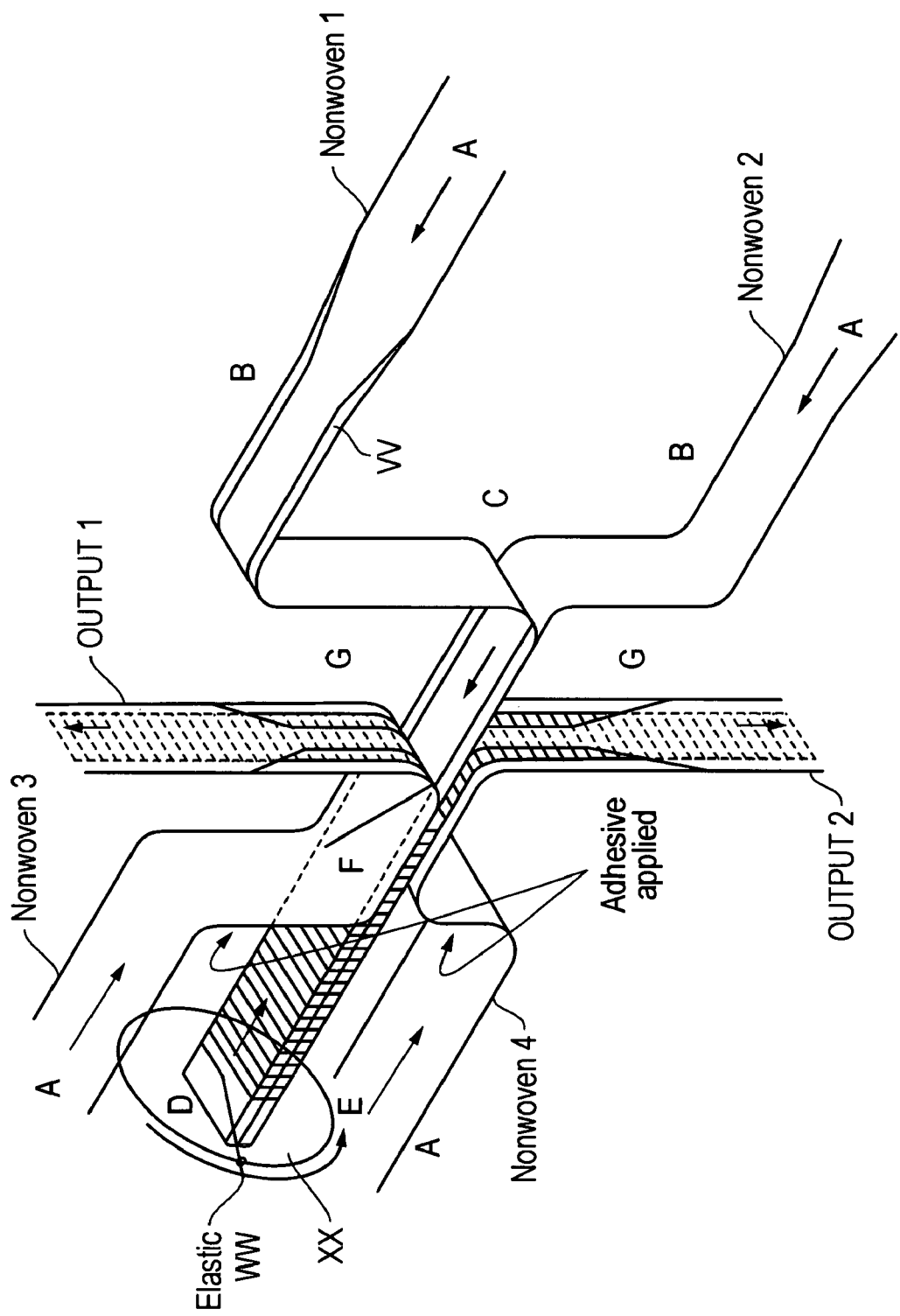
FIG. 13 is a simplified process illustration of making the elastic composite according to the invention.
Figure 14:
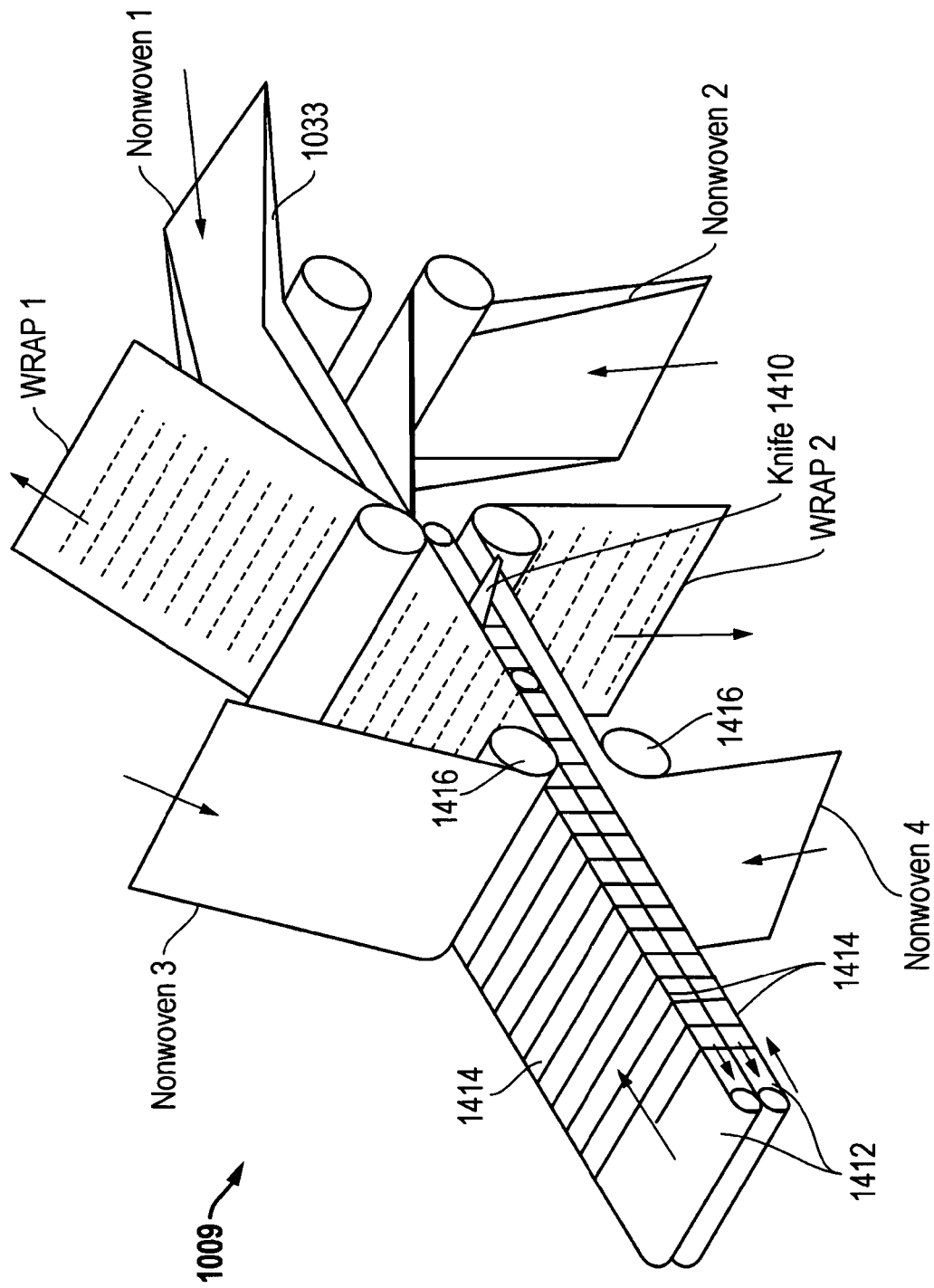
FIG. 14 is a detail view of a conveyor assembly for the system of FIG. 1 according to the invention.

FIGS. 11 and 12 provide alternate views of the spinning head assembly 1007 and conveyor assembly 1009. As discussed above, the conveyor assembly 1009 receives four separate webs of non-woven materials and outputs two webs 1031 of elastic composite. FIGS. 13 and 14 are provided to further illustrate the process of making the elastic composite according to the invention. These figures, more particularly FIG. 13, illustrates the paths taken by the non-woven web materials to and from the conveyor assembly 1009.

Referring to FIG. 13, reference letters A-G are used to refer to stages in the process and in conjunction with the description of the process. As discussed above, non-woven raw material webs are fed into the process at stage A. These webs provide four separate non-woven web inputs into the process. Non-woven webs 1 and 3 are combined to make an elastic composite output 1 (i.e., referred to in the Figures as the WRAP output). Non-wovens 2 and 4, which are both on the downside of the spinning head assembly 1007 and conveyor assembly 1009, combine to make a second elastic composite output 2 (i.e., WRAP 2).

At stage B, non-woven webs 1 and 2 are folded prior to being directed to the conveyor assembly 1009. A predetermined width of non-woven is folded over each side of the web to make two folded flaps VV. The width of the flap VV determines the width of the dead zone or non-elasticized region described previously, while the width of the non-woven, after folding, determines the width of the elasticized region. At stage C, the non-woven webs 1 and 2 are fed into the conveyor assembly 1009, in particular into the middle or inside of the conveyor assembly 1009 with the folded side of each web facing the outside of or away from the conveyor assembly 1009. It should be noted that at this stage C, non-woven webs 1 and 2 are not bonded together. The conveyor 1009 then feeds the non-woven webs 1 and 2 towards the spinning head assembly 1007. At stage D, the non-woven webs 1 and 2 have traveled almost the length of the conveyor assembly 1009 and progresses into the spinning path of spinning head assembly 1007 and intersecting the "spinning" vertical plane XX of the elastic strand WW. Further, at the end of the conveyor assembly 1009, the webs 1 and 2 are directed away from each other and onto the outside of the conveyor 1009 and away from the spinning head 1007. Non-woven web 1 turns up on the upper side of the conveyor assembly 1009, while non-woven web 2 travels along the lower side of the conveyor assembly 1009. At stage E, an elastic strand WW is wound around the folded non-woven webs 1 and 2, as these webs pass through the spinning head and the vertical plane XX. The elastic strand WW is applied to the moving webs 1 and 2 cross-directionally to the direction of the moving web. The movements of the webs 1 and 2 away from within the spin cylinder 1017 draws the "wrapped" elastic strand out of the spin cylinder 1017.

Now turning to non-woven webs 3 and 4, these webs are provided to the conveyor assembly 1009 with adhesive applied on one side (i.e., applied by the adhesive applicator 1013). At stage F, the non-woven webs 3 and 4 are brought into contact with webs 1 and 2, respectively, and the elastic strands WW. As a result, the webs 1 and 3 sandwich elastic strands WW on the upper side of the conveyor assembly 1009, and non-woven webs 2 and 4 sandwich elastic strands WW on the under side of the conveyor assembly 1009. The elastic strands WW run between the two non-woven elastic non-woven composite (cross-direction), but is then cut by a knife (see knife 1410 in FIG. 14, as described below), thereby separating the two wrapped composites. At stage G, the composites 1 and 2 are fed away from the conveyor assembly 1009 and the folded flaps on webs 1 and 2 become unfolded, with guiding, to form a flat non-woven composite. Subsequently, the composites are guided from the spinning head assembly 1007 and conveyor assembly 1009 and into further processes. As shown in FIG. 10, the elastic output webs arrives via a system of rollers onto an elastic composite output reel 1005.

FIG. 14 provides an alternate view of the conveyor assembly 1009. This Figure further illustrates the movement of non-woven webs 1-4, and the application of elastic strands in a generally mutually parallel pattern and generally spaced apart from one another. After cutting of the elastic with the knife 1410, two elastic composites are directed away from the conveyor assembly 1009. It should also be noted that the inventive system advantageously allows for improved control of the stretch of the elastic strands.

As shown in FIGS. 11 and 14, the conveyor assembly 1009 preferably includes two web moving platforms 1412 which are juxtapositioned so as to provide an interface therebetween. Each web moving platform 1412 includes a continuous belt 1414 supported about a plurality of rollers 1416 so as to be capable of reciprocal motion. The two web moving platforms 1412 are generally the same length and juxtapositioned so as to accommodate the non-woven webs 1 and 2 therealong from one end to the other end. Preferably, a roller 1416 is situated about midway between the ends of the web moving platform so as to deliver the non-woven webs 3 and 4 respectively to the web moving platform.

As shown in FIG. 10 and also FIG. 14, the spinning head assembly 1007 is positioned about and in the vicinity of one end of the conveyor assembly 1009. In operation, the spinning head 1017 spins about the vertical plane XX which intersects the ends of the web moving platforms 1412 so as to deliver the elastic strands WW around and about both web moving platforms 1412. In operation, the first and second non-woven move along the outside or exposed surfaces or sides of the web moving platforms 1412 and receives the elastic strands WW delivered by the spinning head 1017. By way of its movement away from the spinning head 1017, the moving web draws the continuous elastic strand WW from the spinning head 1017.

By pre-folding the two non-woven webs that are fed to the inside of the conveyor assembly 1009, it is possible to create an elastic composite with cross directional stretch having non-elasticized regions ("dead zones") along each edge. The width of the central elasticized region is fixed to the width of the conveyor platform 1412. The width of the non-elasticized regions or dead zones is determined by the width of the fold VV. The fold VV in the non-woven is preserved by the conveyor assembly 1009 during application of the elastic element and is applied in such a way that the folded edge of the non-woven is not in contact with the elastic element WW. The fold VV is then allowed to open after the composite exits the conveyor assembly 1009 to provide a flat elastic composite with non-elasticized regions. By altering the alignment of the materials as it enters the conveyor assembly 1009 or by changing the widths of the materials used it is possible to create various composite designs.

The above-described process provides an elastic composite with cross directional stretch properties. The process also provides non-elasticized regions on either latitudinal side of the central elasticized zone of the composite. For the purposes of the description the term "non-woven" is used to describe the principal material used in the construction of the elastic composite. However, it should be noted that this invention is not limited to non-woven materials but may be applied to any material that is available in the form of a continuous sheet. Other materials suitable for this application include PE film, PE film/non-woven laminates and tissue.

Figure 15:
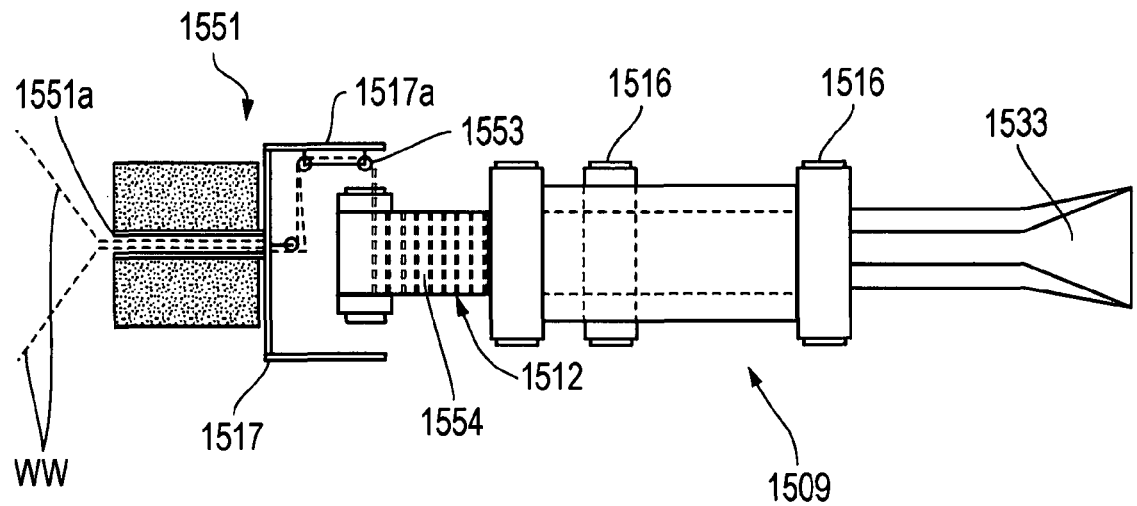
FIG. 15 is a top view of an alternative elastic element applicator assembly for use with the system of FIG. 10, according to the invention.

FIG. 15 illustrates a conveyor assembly 1509 and an elastic element applicator in the form of a spinning head assembly 1507, in accordance with an alternative embodiment of the present invention. As will be understood by one skilled in the art, the spinning head assembly 1507 is operated to convey or transmit elastic strands onto a web moving platform 1512 of the conveyor assembly 1509. As before, the conveyor assembly 1509 preferably employs two web moving platforms 1512, which are juxtapositioned so as to provide an interface therebetween. The conveyor assembly 1509 is similar to that illustrated in FIGS. 10 and 11.

On the other hand, the conveyor assembly 1509 is operated differently in that more than one elastic strand WW is applied onto and about the web moving platforms 1512 at one time. The spinning head assembly 1507 includes a spinning head in the form of a spin bracket 1517 having a plurality of arms 1517a. The spin bracket 1517 receives elastic strands 1553 from a shaft 1551a of a motor 1551. The motor 1551 feeds the two lines of elastic strands 1553 to the spin bracket 1517, and the two feeds of elastic strands 1553 are guided together through the spinning head assembly 1517 (where the two lines twist together). As shown in FIG. 15, the two strands 1533 are moved about a v vertical plane then delivered, together, onto a nonwoven web 1544 moving horizontally on the web moving platform 1512. Preferably, both lines of elastic strand 1553 are fed onto the same arm 1517a of the spinning bracket assembly 1517 (rather than on opposite sides). In this way, the separate feeds or lines of elastic strands 1553 are prevented from twisting together and possibly breaking.

By applying two lines (or more) of elastic strands onto the moving nonwoven web, the speed of the manufacturing process is increased. Specifically, the speed at which the composite is manufactured may be increased by up to 100%, without increasing the speed at which the spinning head assembly is spinning and without changing the overall number of elastic strands in the final composite. Table 1 below provides two examples of the result of a process of applying the elastic strands WW onto a nonwoven web, according to the present invention. The spinning head assembly 1517 operates at the same rotational speed in both processes. However, the pitch (i.e., the separation between elastic strands WW) is doubled for the alternative process (wherein a pair of elastic strands are applied to the nonwoven web). By employing the alternative process, the total machine output is also doubled (i.e., from 40 m/min of composite to 80 m/min). In both examples, the overall amount or length of elastic strands WW utilized or applied to the composite is generally the same. Consequently, the final composite produced by both subprocesses have the same, or at least, similar tensile characteristics.

TABLE 1

| Spin head speed | Pitch (elastic separation) | No of elastic strands fed into spin head | Total machine output (two webs of composite) |
|---|---|---|---|
| 8,000 rpm | 2.5 mm | 1 | 40 m/min |
| 8,000 rpm | 5 mm | 2 | 80 m/min |

It will be apparent to one skilled in the relevant art, upon reading the present description and/or reviewing the accompanying drawings, that the alternative subprocess described above may be modified to feed or apply a different number of elastic strands onto the nonwoven web. That is, three or more elastic strands may be fed through the spinning head assembly and applied to the nonwoven web.

Moreover, it is contemplated that the elastic strands may be separated inside the spin head and directed independently to opposite sides of the nonwoven web. In such a case, it is preferred that the assembly 1507 that includes the elastic bobbins/reel and tensioners and guides the elastic strands into the motor 1551 (or more appropriately, the motor shaft 1551a), is rotated at the same speed and in the same direction as the spin head 1517. In this way, the risk of twisting of the strands together inside the spin head 1517 is minimized.

The foregoing description of the present invention has been presented for purposes of illustration and description. It is to be noted that the description is not intended to limit the invention to the various apparatus and processes disclosed herein. Various aspects of the invention as described above, may be applicable to other types of disposable absorbent articles and garments, and processes for making the same. For example, the elastic composite described above, may be incorporated in other disposable absorbent garments such as training pants, etc. or in other areas or as other components of the garment. Moreover, the various aspects of process described in respect to FIGS. 10-16 may be utilized to produce compositions, garments and articles other than those described herein. Such variations of the invention will become apparent to one skilled in the relevant consumer products art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A method of making an elastic composite for incorporation into a disposable absorbent garment, said method comprising the steps of:
    conveying a first sheet of material on a web moving platform such that the front sheet is moved with the moving platform;
    spinning a section of a continuous strand of elastic element three hundred and sixty degrees about the moving platform and the first sheet on the platform, thereby applying the section of elastic element onto the first sheet along a direction generally transverse to a moving first sheet;
    cutting the section of elastic element to sever the section from the continuous strand; and
    repeating the spinning and cutting steps such that a plurality of spaced apart elastic elements are applied on the first sheet.

2. The method of claim 1, further comprising the step of applying a second sheet of material onto the first sheet having a plurality of elastic elements applied thereon, thereby providing a web of elastic composite having at least two sheets of material and a plurality of elastic elements sandwiched therebetween.

3. The method of claim 1, wherein the applying step includes applying a section of tensioned elastic element onto the moving first sheet such that the section of elastic element is retained thereby and the moving first sheet draws the strand of elastic element from the spinning assembly.

4. The method of claim 1, further comprising positioning a spinning assembly relative to the platform for receiving the continuous strand and spinning an end section of the continuous strand about a plane that intersects the platform, wherein the spinning step includes operating the spinning assembly to spin the section of continuous strand about the plane.

5. The method of claim 4, further comprising the steps of:
    feeding a continuous strand of the elastic element to the spinning assembly from a feed source spaced apart from the spinning assembly, whereby the spinning step draws the continuous elastic strand from the feed source.

6. The method of claim 4, wherein the spinning assembly includes a spin head positioned for spinning about the platform, said method further comprising the steps of:
    positioning a feed source of the continuous elastic strand in spaced apart relation to the spin head; and
    feeding a continuous strand from the feed source to the spin head, whereby the spinning step draws the section of continuous elastic strand from the feed source.

7. The method of claim 1, wherein the spinning step applies a plurality of elastic strands strictly on an outward face of the first sheet in mutual generally parallel relation and in transverse relation to the first sheet moving direction.

8. The method of claim 1, further comprising the step of conveying a second sheet of material spaced apart from the first sheet, whereby the spinning step applies the section of elastic element onto the first sheet and the second sheet along a direction generally traverse to a moving second sheet and the cutting step includes cutting the section of elastic element at two places to sever two elastic strands from the continuous elastic strand.

9. The method of claim 8, wherein each of the first and second webs are moved by a pair of juxtaposed conveying platforms that intersect a plane of about which the elastic element is spun, said method further comprising the steps of first conveying the first and second sheet on the platforms in an initial sheet moving direction opposite of the first sheet moving direction, whereby the first and second sheets are redirected in the first sheet moving direction upon reaching one end of the platforms.

10. The method of claim 1, wherein the spinning step includes spinning an end section of a continuous strand of elastic element generally about a plane, said conveying step including moving the first sheet into and generally past the plane and redirecting the first sheet in the sheet moving direction so that the first sheet returns to intersect the plane whereby the section of elastic element is applied onto the returning first sheet.

11. The method of claim 4, wherein the conveying step includes directing the first sheet of material from a first side of the plane, and wherein the feed source is positioned on a second side of the plane, spaced apart from the plane, the method further comprising the step of:
feeding a strand of the elastic element from the feed source to the spinning assembly.

12. The method of claim 11, wherein the feeding step includes drawing the elastic strand from the feed source to a spin axis of the spinning assembly.

13. The method of claim 12, wherein the conveying step includes directing the sheet of material substantially linearly toward the spin axis from the first side of the plane.

14. The method of claim 13, wherein the sheet of material and the elastic strand being drawn are both directed along a direction coincident with the axes of the spinning assembly and the plane.

15. A method of making an elastic composite for incorporation into a disposable absorbent garment, said method comprising the steps of:
spinning an end section of a continuous strand of elastic element generally three hundred and sixty degrees about a plane; and
conveying a first web of material, including moving the first web of material into and generally past the plane and redirecting the first web in a web moving direction such that the first web returns to intersect the plane, whereby the section of elastic element is applied onto the returning first web along a direction generally transverse to the web moving direction.

16. The method of claim 15, wherein the conveying step includes conveying the first web on a platform supported by a continuous belt moveable about a looped path, whereby the looped path intersecting the plane at two places.

17. The method of claim 15, wherein the conveying step includes directing the sheet of material from a first side of the plane toward a spin axis of the plane.

18. The method of claim 15, wherein the conveying step includes moving the first web along a first web moving direction into and generally past the plane and then redirecting the first web in a web moving direction that is a reverse of the first web moving direction.

19. The method of claim 15, further comprising the steps of:
feeding the continuous strand of the elastic element to the spinning assembly from a feed source spaced apart from the spinning assembly, whereby the spinning step draws the continuous elastic strand from the feed source.

20. The method of claim 15, wherein the conveying step includes directing the first web of material from a first side of the plane, and wherein the feed source is positioned on a second side of the plane, spaced apart from the plane, the method further comprising the step of:
feeding the continuous strand of elastic element from the feed source to the spinning assembly, whereby the spinning assembly receives the continuous strand.

21. The method of claim 20, wherein the feeding step including drawing the elastic strand from the feed source along a substantially linear path to a spin axis of the spinning assembly; and
wherein the conveying step includes directing the sheet of material substantially linearly toward the spin axis from the first side of the plane.

22. A method of making an elastic composite for incorporation into a disposable absorbent garment, said method comprising the steps of:
providing a web moving platform for moving a sheet of material;
positioning a spinning assembly in space apart relation to the web moving platform, the spinning assembly being configured to spin a section of a continuous strand of elastic element generally about a plane intersecting the platform;
positioning a feed source of elastic strand at a location spaced from the spinning assembly;
feeding the spinning head assembly a continuous elastic strand from the feed source;
conveying a first sheet of material in a web moving direction such that the first sheet intersects the plane, including moving the web moving platform such that the first sheet moves therewith;
operating the spinning assembly to spin the end section of continuous elastic strand three hundred and sixty degrees about the plane and about the moving platform and web thereon, thereby applying the end section of elastic strand onto the first sheet along a direction generally transverse to the web moving direction; and
wherein the conveying step includes directing the first sheet of material from a first side of the plane toward a spin axis of the spinning assembly, and wherein the feed source is positioned on a second side of the plane, spaced apart from the plane, such that the feeding step further includes drawing the elastic strand from the feed source toward the spin axis.

23. The method of claim 22, wherein the spinning step draws a continuous elastic strand from the feed source.

24. The method of claim 22, wherein the applying step includes retaining the end section on the moving first sheet, whereby the moving first sheet draws the end section from the plane.

25. The method of claim 22, wherein the web moving platform is supported about a continuous belt and moveable with the belt about a looped path, and wherein the spinning step includes spinning the end section about the belt and about the looped path.

26. The method of claim 22,
wherein the feeding step includes drawing the continuous elastic strand from the feed source along a substantially linear path to the spin axis of the spinning assembly; and
wherein the conveying step includes directing the sheet of material substantially linearly toward the spin axis from the first side of the plane.

27. The method of claim 22, wherein the conveying step includes moving the first sheet on the moving platform with an exposed outward planar surface and an inward planar surface opposite the exposed planar surface, the operating step including spinning the section of elastic strand about the plane and about the first web, thereby applying the section of elastic element, in tension, onto the exposed outward planar surface of the first web along a direction generally transverse to said web moving direction but spacing the elastic element from the inward planar surface, the method further comprising the steps of:

continuing to convey the first sheet away from the plane with applied sections of elastic elements retained on the exposed outward planar surface; and cutting the applied sections of elastic element at opposing ends, thereby separating individual elastic elements from the continuous strand and providing a sheet of elastic composite having a layer of the sheet material and a plurality of spaced apart elastic elements retained only on the exposed outward planar surface.

* * * * *

UNITED STATES PATENT AND TRADEMARK OFFICE
CERTIFICATE OF CORRECTION

| | | |
|---|---|---|
| PATENT NO. | : 7,740,727 B2 | Page 1 of 1 |
| APPLICATION NO. | : 11/982349 | |
| DATED | : June 22, 2010 | |
| INVENTOR(S) | : Chang et al. | |

It is certified that error appears in the above-identified patent and that said Letters Patent is hereby corrected as shown below:

On The Title Page

Please include Item (60) Related U.S. Application Data: the data should recite -- Continuation of U.S. Application No. 11/021,424, filed on December 23, 2004, now U.S. Patent No. 7,361,246, which claims the benefit of U.S. Provisional Application No. 60/532,480, filed on December 24, 2003. --

Signed and Sealed this
Seventh Day of June, 2011

David J. Kappos
*Director of the United States Patent and Trademark Office*